United States Patent
Oh et al.

(10) Patent No.: US 11,304,388 B2
(45) Date of Patent: Apr. 19, 2022

(54) **METHOD FOR PROMOTING GROWTH AND BIOACTIVE SUBSTANCES OF *CREPIDIASTRUM DENTICULATUM***

(71) Applicants: Seoul Viosys Co., Ltd., Ansan-si (KR); INDUSTRY-UNIVERSITY COOPERATION FOUNDATION OF CHUNGBUK NATIONAL UNIVERSITY, Cheongju-si (KR)

(72) Inventors: Myung Min Oh, Cheongju-si (KR); Song Yi Park, Cheongju-si (KR); Jin Hui Lee, Cheongju-si (KR); Ji Hoon Bae, Cheongju-si (KR); Jong Hyun Koo, Ansan-si (KR)

(73) Assignees: Seoul Viosys Co., Ltd., Ansan-si (KR); INDUSTRY-UNIVERSITY COOPERATION FOUNDATION OF CHUNGBUK NATIONAL UNIVERSITY, Cheongju-si (KR)

( * ) Notice: Subject to any disclaimer, the term of this patent is extended or adjusted under 35 U.S.C. 154(b) by 666 days.

(21) Appl. No.: 16/097,139

(22) PCT Filed: Apr. 26, 2017

(86) PCT No.: PCT/KR2017/004422
§ 371 (c)(1),
(2) Date: Oct. 26, 2018

(87) PCT Pub. No.: WO2017/188719
PCT Pub. Date: Nov. 2, 2017

(65) Prior Publication Data
US 2019/0150378 A1    May 23, 2019

(30) Foreign Application Priority Data

Apr. 28, 2016  (KR) .................... 10-2016-0052279
Apr. 28, 2016  (KR) .................... 10-2016-0052284
Apr. 25, 2017  (KR) .................... 10-2017-0053079

(51) Int. Cl.
*A01G 7/04*    (2006.01)
*A01G 22/60*   (2018.01)
*A01G 3/00*    (2006.01)

(52) U.S. Cl.
CPC .............. *A01G 22/60* (2018.02); *A01G 3/00* (2013.01); *A01G 7/04* (2013.01); *A01G 7/045* (2013.01)

(58) Field of Classification Search
CPC ........ A61K 36/28; A01G 22/00; A01G 22/15; A01G 22/60; A01G 7/00; A01G 7/04; A01G 7/045; A01G 7/06
See application file for complete search history.

(56) References Cited

FOREIGN PATENT DOCUMENTS

| KR | 10-2010-0091356 | 8/2010 |
| KR | 10-2013-0051846 | 5/2013 |

(Continued)

OTHER PUBLICATIONS

Sang-Uk Chon "Shading Effect on Plant Growth and Physiological Activity of Youngia sonchifolia Grown in Plastic House", Korean Journal Weed Science, 2010, vol. 30, No. 3; pp. 215-224.

(Continued)

*Primary Examiner* — Peter M Poon
*Assistant Examiner* — Danielle A Clerkley
(74) *Attorney, Agent, or Firm* — H.C. Park & Associates, PLC

(57) ABSTRACT

A method for promoting growth and bioactive substances of *Crepidiastrum denticulatum* including performing a stress treatment on *Crepidiastrum denticulatum* during cultivation thereof, in which the stress treatment includes at least of applying visible light, drying, exposing to low temperature, irradiating ultraviolet rays, and applying a chemical elicitor.

24 Claims, 29 Drawing Sheets

(56) References Cited

FOREIGN PATENT DOCUMENTS

| KR | 10-2014-0014498 | | 2/2014 | |
|---|---|---|---|---|
| KR | 10-2014-0097702 | | 8/2014 | |
| KR | 20140097702 | A * | 8/2014 | ............ A01G 22/00 |
| KR | 10-1439009 | | 9/2014 | |
| WO | WO1999025191 | A1 * | 5/1999 | ............ A01N 37/10 |

OTHER PUBLICATIONS

International Search Report dated Aug. 8, 2017, in International Application No. PCT/KR2017/004422.
Chinese Office Action dated Jun. 11, 2020 in Chinese Application No. 201780026511.2.
Luo Qun et al., The Effect of Drought Stress on Soluble Proteins in Nine Compositae Weeds, Journal of Sichuan Normal University, May 2006, vol. 29, No. 3.
Yang Dong et al., Effect of Temperature Stress on Propanediai and Soluble Suger Contents in Ten Compositae Weeds, Journal of Sichuan Normal University, May 2007, vol. 30, No. 3.
Wang Chun-Li et al., Research Progress of Signal Transduction Pathway and Regulation of Secondary Metabolism in Plant Induced by Exogenous Stimulus, Acta Botanica Boreali-Occidentalia Sinica, 2009, pp. 1055-1065, vol. 29.
Chinese Office Action dated Nov. 24, 2021, in Chinese Patent Office for Chinese Patent Application No. 202011171805.4. (with English Translation).
"Effect of Plant Growth Regulator and Water Stress On Root Crown Thickening Growth and Seedling Growth of Paeonia OSTII", Agriculture Science and Technology, 2011, pp. 1-44, Chinese Doctoral Dissertations & Master's Thesis Full Text Database, China.
Gerda M. Nitz and Wilfried H. Schnitzler, "Effect of PAR and UV-B Radiation on the Quality and Quantity of the Essential Oil in Sweet Basil (*Ocimum basilicum L.*)", 2004, pp. 375-382, vol. 659, Acta Hort., Germany.
Korean Office Action dated Feb. 3, 2022, in Korean Patent Office for Korean Patent Application No. 10-2017-0053079 (with English Translation).
Sang-Uk Chon, "Shading Effect on Plant Growth and Physiological Activity of Youngia sonchifolia Grown in Plastic House", 2010, pp. 215-224, Chosun University, Republic of Korea.
Mi-Young Park, "Infrastructure construction of "cultivation manual" for functional crops by growth stage", 2015, DigitalTimes, Republic of Korea, (with English Translation).

* cited by examiner

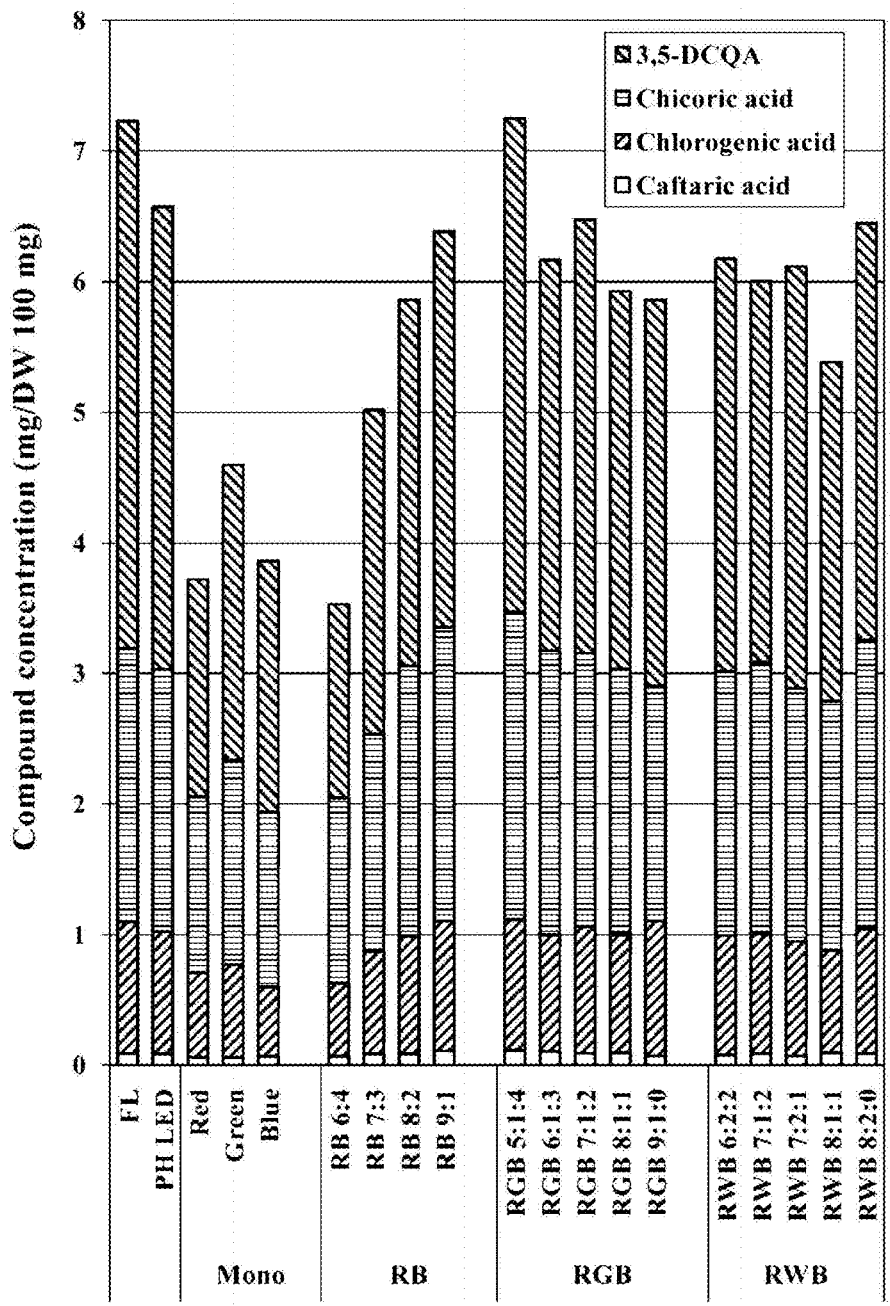

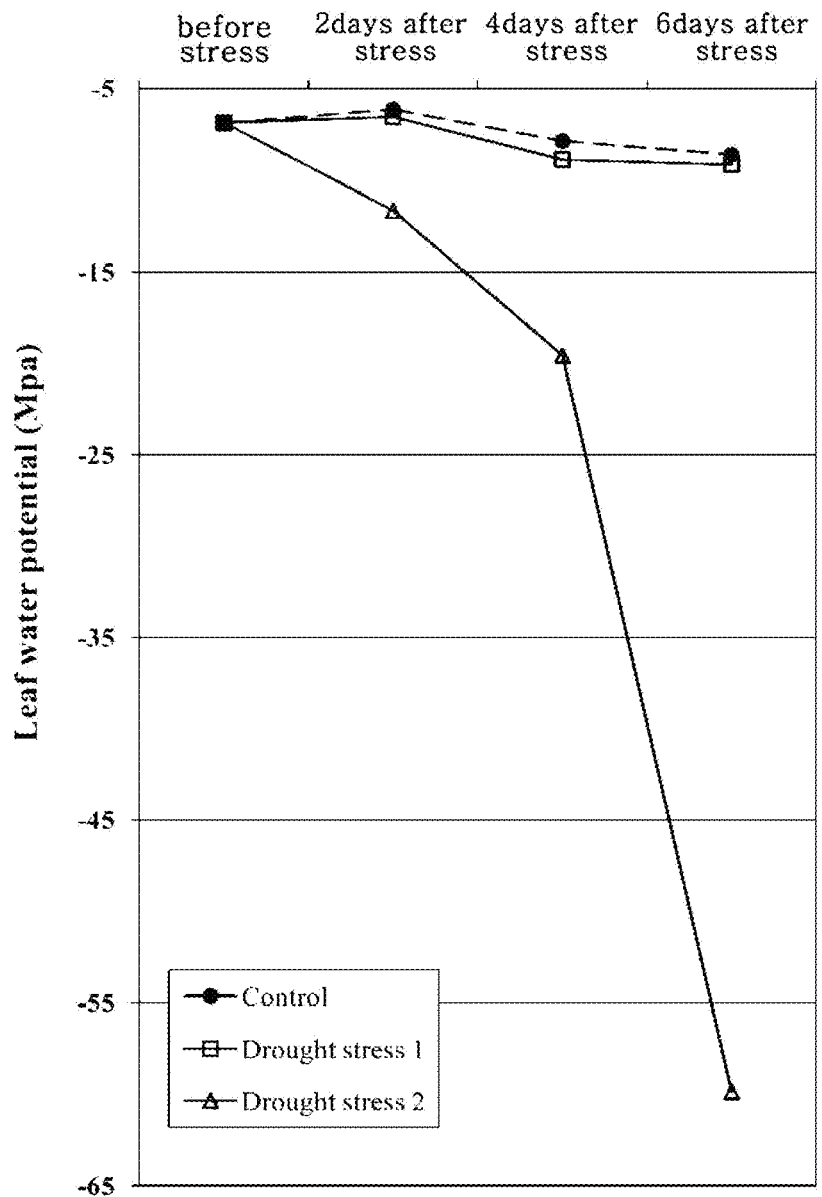

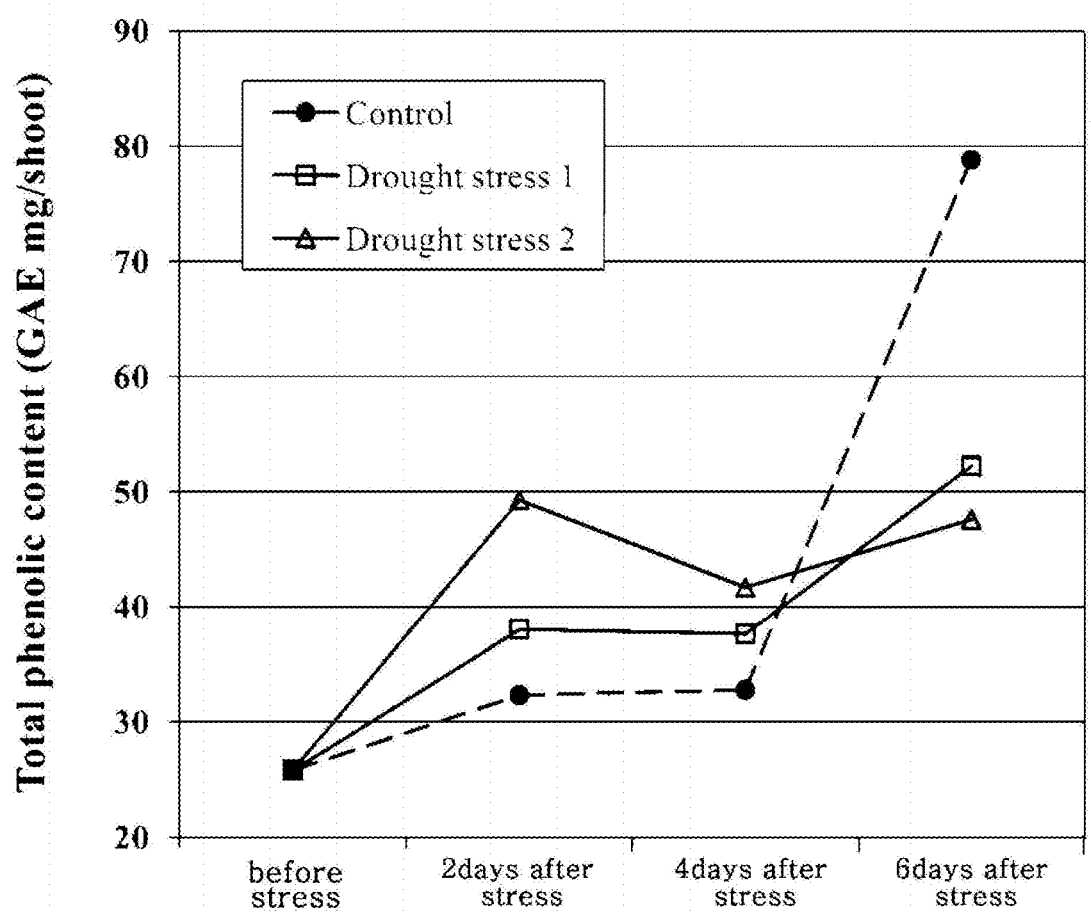

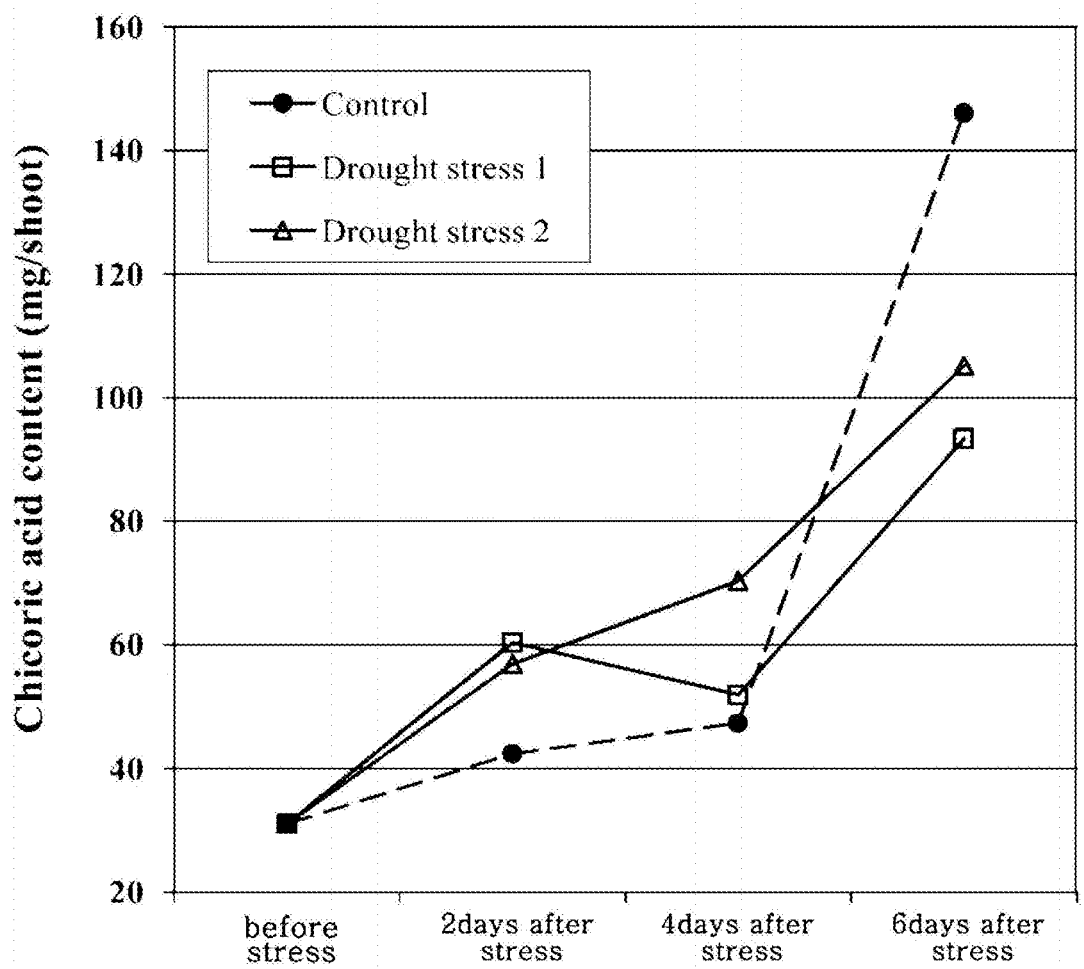

METHOD FOR PROMOTING GROWTH AND BIOACTIVE SUBSTANCES OF *CREPIDIASTRUM DENTICULATUM*

CROSS REFERENCE TO RELATED APPLICATIONS

This application is the National Stage Entry of International Patent Application No. PCT/KR2017/004422, filed on Apr. 26, 2017, and claims priority from and the benefit of Korean Patent Application No. 10-2016-0052279, filed on Apr. 28, 2016, Korean Patent Application No. 10-2016-0052284, filed on Apr. 28, 2016, and Korean Patent Application No. 10-2017-0053079, filed on Apr. 25, 2017, each of which is incorporated by reference for all purposes as if fully set forth herein.

BACKGROUND

Field

Exemplary embodiments of the invention relate to a method for promoting growth and bioactive substances of *Crepidiastrum denticulatum*, which is a plant of the genus *Crepidiastrum*.

Discussion of the Background

When plants undergo photosynthesis, light used for growth is generally limited to a specific wavelength range. However, since most of the artificial lighting are developed for human vision, there is very little light available for plants even with the same amount of brightness. For example, artificial lighting, which has recently been introduced into plant factories leading urbanization agriculture, requires an artificial light source that has low energy consumption for reducing greenhouse gases, which is the main cause of global warming, and that emits a wavelength band which has the maximum efficiency for photosynthesis in plant growth activity and light color balance for formation of light. In recent years, a plant growth environment that utilizes a light emitting diode (LED) light has been introduced. An LED light is an eco-friendly light with high light efficiency capable of selectively using only a specific wavelength region, as compared to an incandescent light or a fluorescent light which has been used in the past.

An LED has a number of advantages over the incandescent light, such as faster switching, lower energy consumption, longer life, compactness, durability, and reliability, and the like. Thus, a number of researches have been conducted by using LED as a light source for regulating photomorphogenesis and growth of plants (Heo, 2002 Plant Growth Regulation 38: 225-230).

There are few factors in light environment that affects plant growth, such as light intensity, light quality, and day length. Photosynthesis is influenced by the light intensity, and the wavelength range of red light and blue light is effective for growth of plants, and the like. Plants may promote photosynthesis or may achieve photomorphogenesis by specific wavelengths in ultraviolet region or visible light region. In particular, it is known that blue light (400-500 nm) promotes photosynthesis and suppresses stem elongation, red light (600-700 nm) is involved in photosynthesis promotion, flowering and stem elongation, and green light (500-600 nm) plays a supporting role in photosynthesis. Further, it has been found that the far-red light (700-800 nm) is involved in flowering, promoting stem elongation, seed germination control, and ultraviolet ray A and ultraviolet ray B are involved in synthesis of phytochemicals. In addition, flowering time of the plants is determined depending on the day length.

*Crepidiastrum denticulatum* is an annual plant or a biennial plant of the dicotyledon, Sympetalae, Campanulales, *Chrysanthemum* family, and grows in dry places in mountains and fields, and has a height of about 30 to 70 cm. The stem is thin and purple. *Crepidiastrum denticulatum* has branches that spread, and juice comes out when the branches are cut. Leaves on the roots have spatula shapes and drop when flowers bloom. Leaves on the stem are alternately arranged. Further, there is no petiole. The leaf length is about 6-11 cm, the leaf width is about 3-7 cm, and the end is dull. The lower part is wrapped around the stem halfway like an ear, and the edges of the leaf have teeth-shaped sawtooth which are sparsely formed. The flower blooms in about August to September with substantially yellow color, and the cephalization is about 15 mm in diameter and forms in the manner of corymb. When the flower blooms, it grows straight up, and it droops downwardly after the flower drops. An involucre looks like a narrow tub, involucral bracts are arranged in 2 lines with a long elliptical shaped lanceolate, and the lacinia has a line shape in 8 pieces. The fruit is a achene with brown or black color and has 12 ridges. The pappus is white and has a length of about 3.5 mm. The young shoot is eaten as greens. It is known that *Crepidiastrum denticulatum* is distributed in Korea, Japan, China, and Indochina, and contains various functional substances.

The above information disclosed in this Background section is only for understanding of the background of the inventive concepts, and, therefore, it may contain information that does not constitute prior art.

SUMMARY

Exemplary embodiments provide a method for promoting growth of *Crepidiastrum denticulatum*, which is a plant from the genus *Crepidiastrum*, using a light emitting diode (LED).

Exemplary embodiments also provide a method for promoting bioactive substances of *Crepidiastrum denticulatum*, using external stress.

A method for promoting growth and bioactive substances of *Crepidiastrum denticulatum* according to an exemplary embodiment includes performing a stress treatment on *Crepidiastrum denticulatum* during cultivation thereof, in which the stress treatment includes at least of applying visible light, drying, exposing to low temperature, irradiating ultraviolet rays, and applying a chemical elicitor.

The visible light may be at least one of white light, red light, green light, and blue light.

The visible light may be one monochromatic light of red light, green light, and blue light.

The visible light may include mixed light having the ratio of at least one of red light:blue light=6:4; red light:blue light=7:3; red light:blue light=8:2; red light:blue light=9:1; red light:green light:blue light=5:1:4; red light:green light:blue light=6:1:3; red light:green light:blue light=7:1:2; red light:green light:blue light=8:1:1; red light:green light:blue light=9:1:0; red light:green light:blue light=7:2:1; red light:white light:blue light=8:1:1; red light:white light:blue light=6:2:2; red light:white light:blue light=7:1:2; and red light:white light:blue light=8:2:0.

The method may further include harvesting *Crepidiastrum denticulatum* on the 6th week after planting *Crepidiastrum denticulatum*, when the visible light is applied during cultivation.

The mixed light may further include a far-red light.

The mixed light may include a red light and a blue light mixed at a ratio of 8:2.

The method may further include harvesting *Crepidiastrum denticulatum* on the 6th week after planting *Crepidiastrum denticulatum*, when the mixed light comprising the far red light is applied during cultivation.

The drying may include stopping watering to *Crepidiastrum denticulatum* for a predetermined period of time.

The method may further include harvesting *Crepidiastrum denticulatum* on the 3rd to 5th days after the drying stress treatment.

The drying may include supplying water to *Crepidiastrum denticulatum* for a predetermined period of time using a wick.

The method may further include harvesting *Crepidiastrum denticulatum* on the 2nd day after the drying stress treatment.

Applying the low temperature may include exposing *Crepidiastrum denticulatum* at 10° C. during one of night time and day time.

The method may further include harvesting *Crepidiastrum denticulatum* on the 3rd to 5th days after the low temperature stress treatment.

The ultraviolet rays may include UV-A.

The method may further include harvesting *Crepidiastrum denticulatum* 8 hours after UV-A is irradiated to *Crepidiastrum denticulatum*.

The ultraviolet rays may include UV-B.

The method may further include harvesting *Crepidiastrum denticulatum* on the 2nd day after UV-B is irradiated to *Crepidiastrum denticulatum*.

UV-B may be irradiated to *Crepidiastrum denticulatum* for 1 hour in every 11 hours during 2 days.

The chemical elicitor may include salicylic acid.

The method may further include harvesting *Crepidiastrum denticulatum* on the 3rd day after the chemical elicitor is sprayed onto *Crepidiastrum denticulatum*.

The growth of *Crepidiastrum denticulatum* may include an increase in at least one of a shoot fresh weight, a shoot dry weight, the number of leaves, a leaf area, a leaf length, and a leaf width of an aerial part.

The bioactive substances of *Crepidiastrum denticulatum* may include a phenolic compound and a chicoric acid.

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the inventive concepts.

FIGS. 5A, 5B, 5C, and 5D are graphs showing results obtained by measuring chicoric acid and phenylpropanoid substance of *Crepidiastrum denticulatum* which is treated with 17 kinds of LED light qualities, respectively.

FIGS. 11A, 11b, and 11C are graphs showing results obtained by measuring the total phenolic compound and chicoric acid included in *Crepidiastrum denticulatum*, water content of *Crepidiastrum denticulatum* leaf, according to two-way drying stress treatment (a wick exposure length of 3 cm using one wick and complete stop of watering), respectively.

DETAILED DESCRIPTION

Objects, specific advantages, and novel characteristics of the present invention will be more clearly understood from the following detailed description taken in conjunction with the accompanying drawings. The exemplary embodiments of the present invention to be described below are provided by way of example so that the idea of the present invention can be sufficiently transferred to those skilled in the art to which the present invention pertains. Therefore, the present invention is not limited to the exemplary embodiments set forth herein but may be modified in many different forms.

Hereinafter, a method of promoting the growth of *Crepidiastrum denticulatum* and a method of promoting bioactive substances of *Crepidiastrum denticulatum* according to exemplary embodiments, such as treating with external stress (hereinafter, referred to as stress) by visible light, drying, low temperature, ultraviolet rays and a chemical elicitor, will be described with reference to the following Examples.

<Example 1> Confirmation of Growth of *Crepidiastrum denticulatum* According to Various LED Light Qualities

*Crepidiastrum denticulatum* was cultivated for 6 weeks after being planted in a closed plant production system under conditions of a temperature of 20° C., a humidity of 60%, a carbon dioxide concentration of 1000 ppm, and 200 µmol/m$^2$/s PPFD. Light quality for cultivating *Crepidiastrum denticulatum* includes red light (R; 654 nm), green light (G; 518 nm), blue light (Blue; B, 455 nm), a combination of red light and blue light (RB), a combination of red light, green light, and blue light (RGB), and a combination of red light, white light (White; W, 456 nm+558 nm) and blue light (RWB). *Crepidiastrum denticulatum* were cultivated under mixed LED environments in which these visible rays are mixed in 17 various ratios.

Figure 1:
FIG. 1 is an image showing appearance comparison of a plant of *Crepidiastrum denticulatum*, depending on various light emitting diode (LED) light qualities.

For example, red light (Red), green light (Green), and blue light (Blue) were used as monochromatic lights. Further, as the mixed LED, light was mixed at the following mixed ratios:red light:blue light=6:4 (RB 6:4); red light:blue light=7:3 (RB 7:3); red light:blue light=8:2 (RB 8:2); red light:blue light=9:1 (RB 9:1); red light:green light:blue light=5:1:4 (RGB 5:1:4); red light:green light:blue light=6:1:3 (RGB 6:1:3); red light:green light:blue light=7:1:2 (RGB 7:1:2); red light:green light:blue light=8:1:1 (RGB 8:1:1); red light:green light:blue light=9:1:0 (RGB 9:1:0); red light:green light:blue light=7:2:1 (RGB 7:2:1); red light:white light:blue light=7:1:2 (RWB 7:1:2); red light:white light:blue light=8:1:1 (RWB 8:1:1); red light:white light:blue light=6:2:2 (RWB 6:2:2); and red light:white light:blue light=8:2:0 (RWB 8:2:0) were used. Further, in order to confirm the growth of *Crepidiastrum denticulatum* according to various LED light qualities, *Crepidiastrum denticulatum* was also cultivated under the environment of fluorescent lamp (FL), and plant husbandry LED (PH LED) used in a conventional plant factory, as shown in FIG. 1.

On the 6th week after the planting, the shoot fresh weight, the shoot dry weight, the number of leaves, the leaf area, the leaf length, and the leaf width of the aerial part were measured on 17 treatment groups. In addition, total phenolic compound, antioxidant capacity, chicoric acid, caftaric acid, chlorogenic acid and 3,5-di-O-caffeoylquinic acid (3,5-DCQA) were analyzed.

Figure 2A:
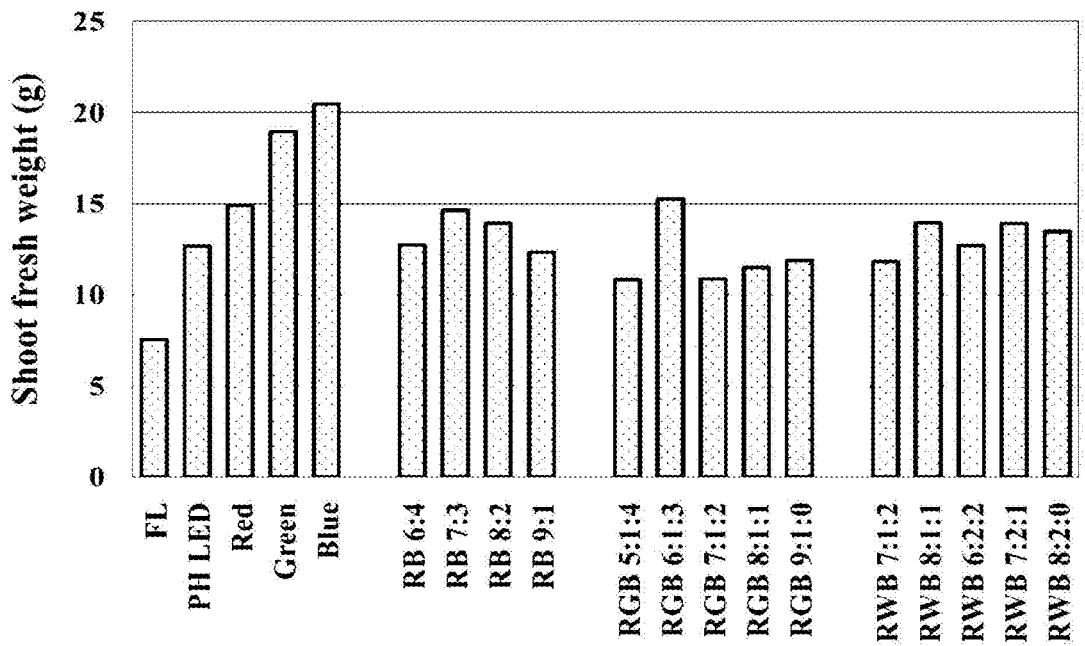
FIGS. 2A and 2B are graphs showing results obtained by measuring shoot fresh weight and shoot dry weight of an aerial part of *Crepidiastrum denticulatum* which is treated with 17 kinds of LED light qualities, respectively.
Figure 2B:
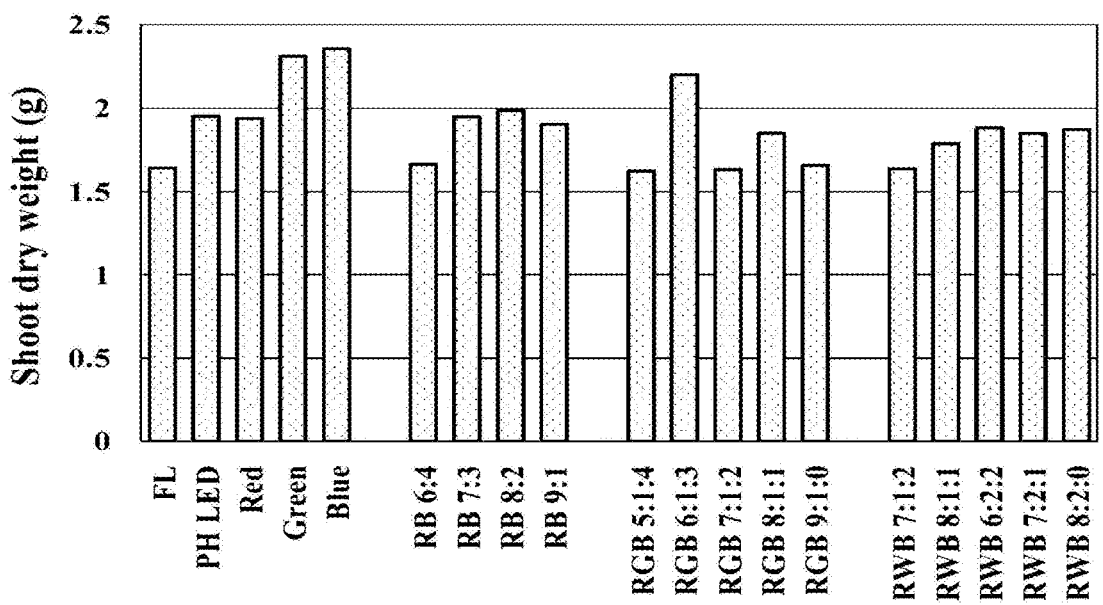
Figure 3A:
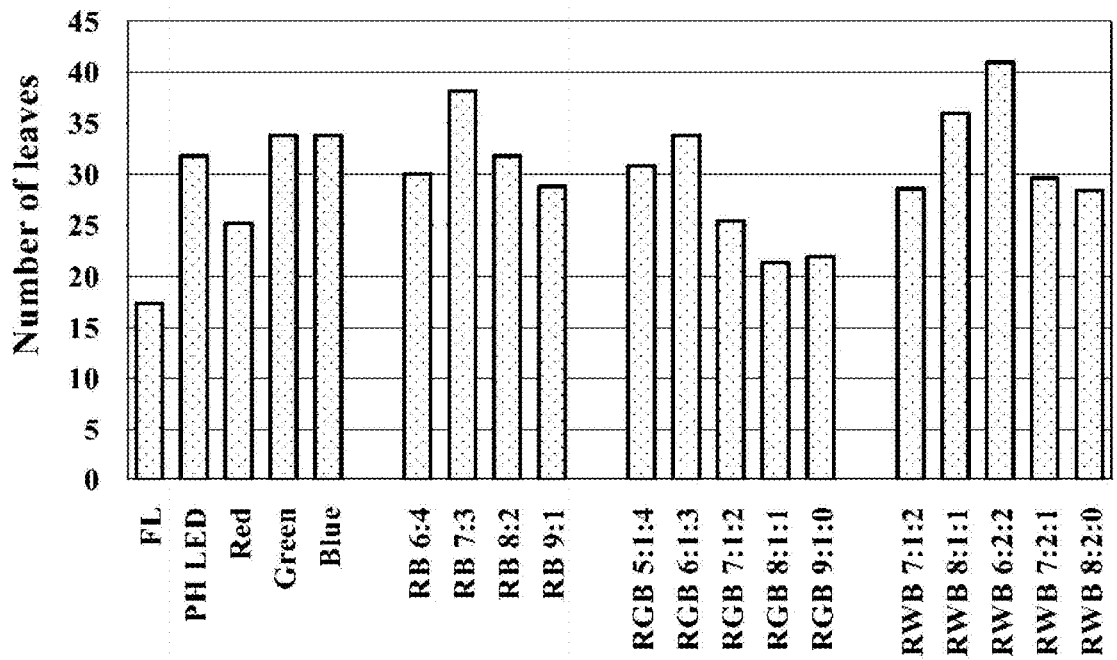
FIGS. 3A, 3B, 3C, and 3D are graphs showing results obtained by measuring number of leaves, leaf area, leaf length, and leaf width of *Crepidiastrum denticulatum* which is treated with 17 kinds of LED light qualities, respectively.
Figure 3B:
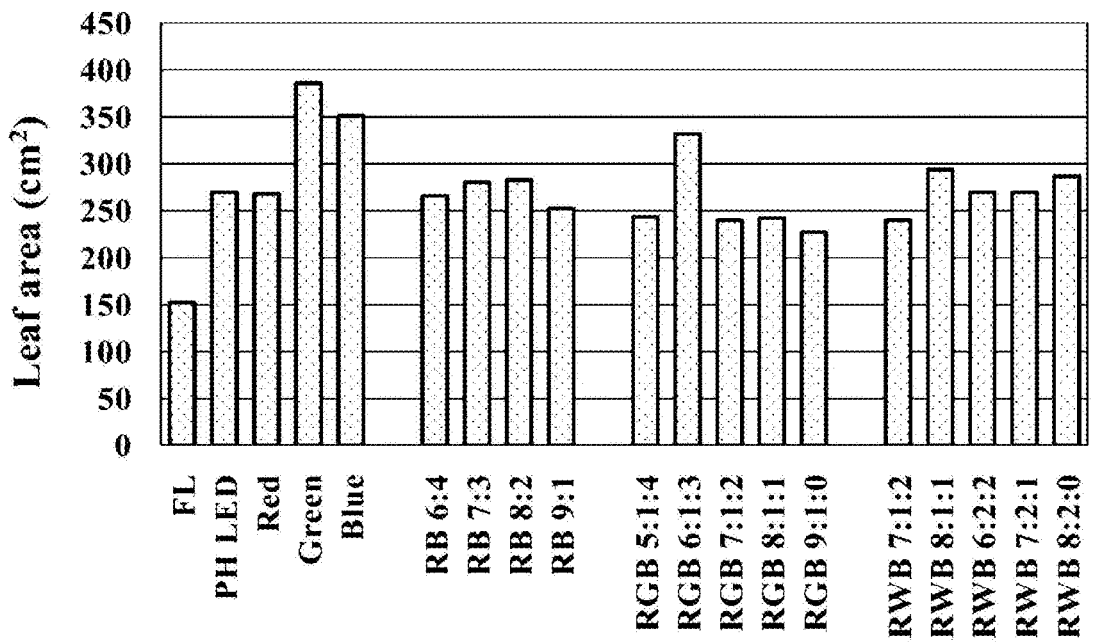
Figure 3C:
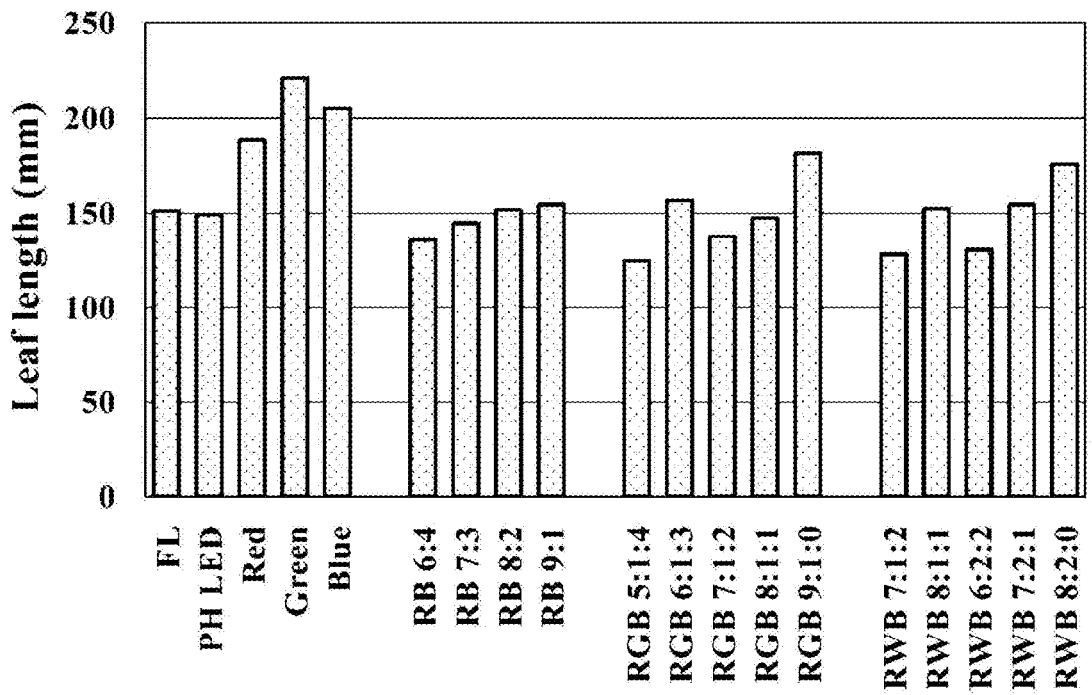
Figure 3D:
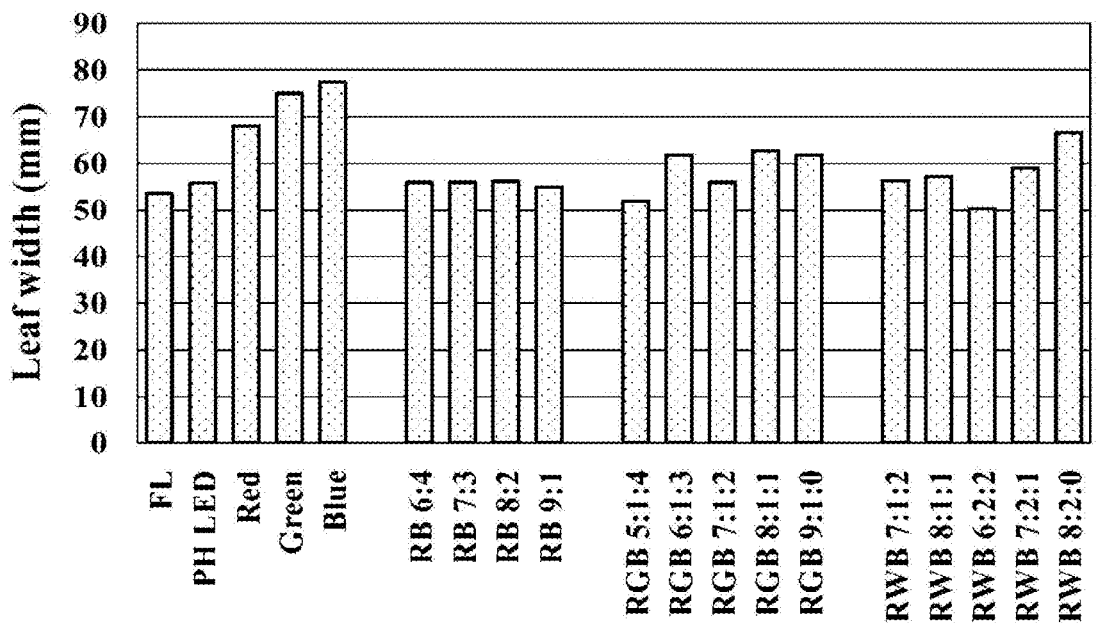
Figure 4A:
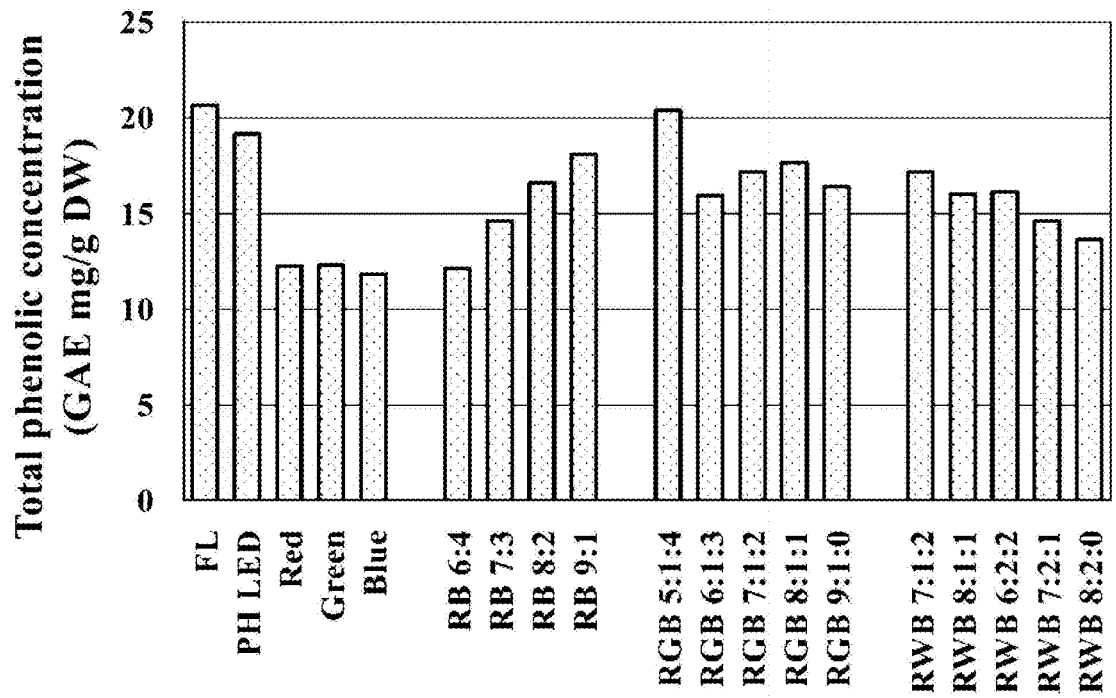
FIGS. 4A, 4B, 4C, and 4D are graphs showing results obtained by measuring a phenolic compound and antioxidation of *Crepidiastrum denticulatum* which is treated with 17 kinds of LED light qualities, respectively.
Figure 4B:
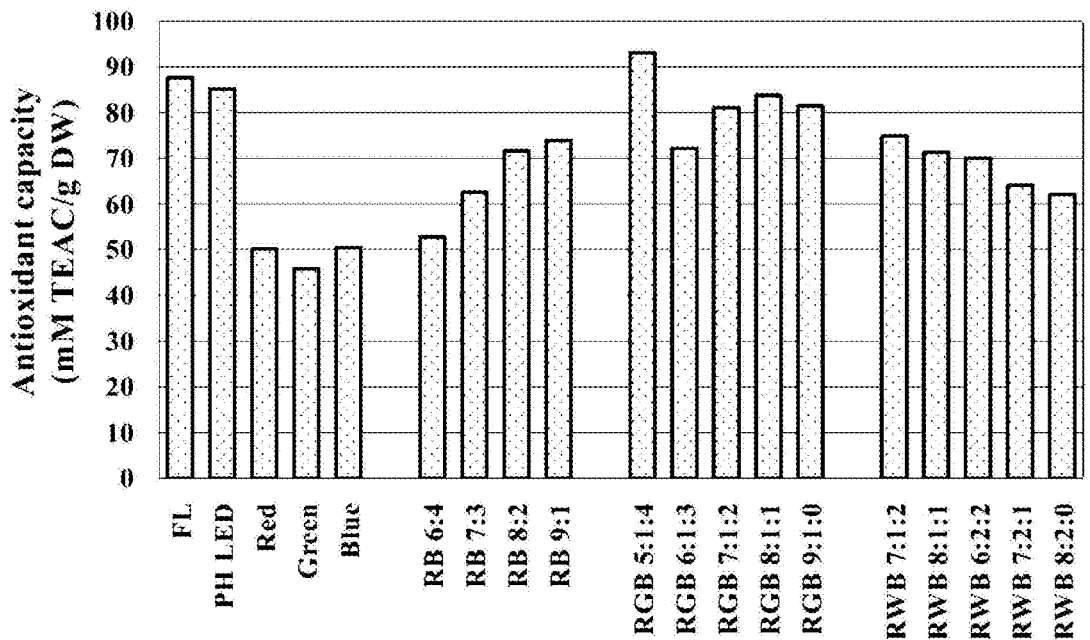
Figure 4C:
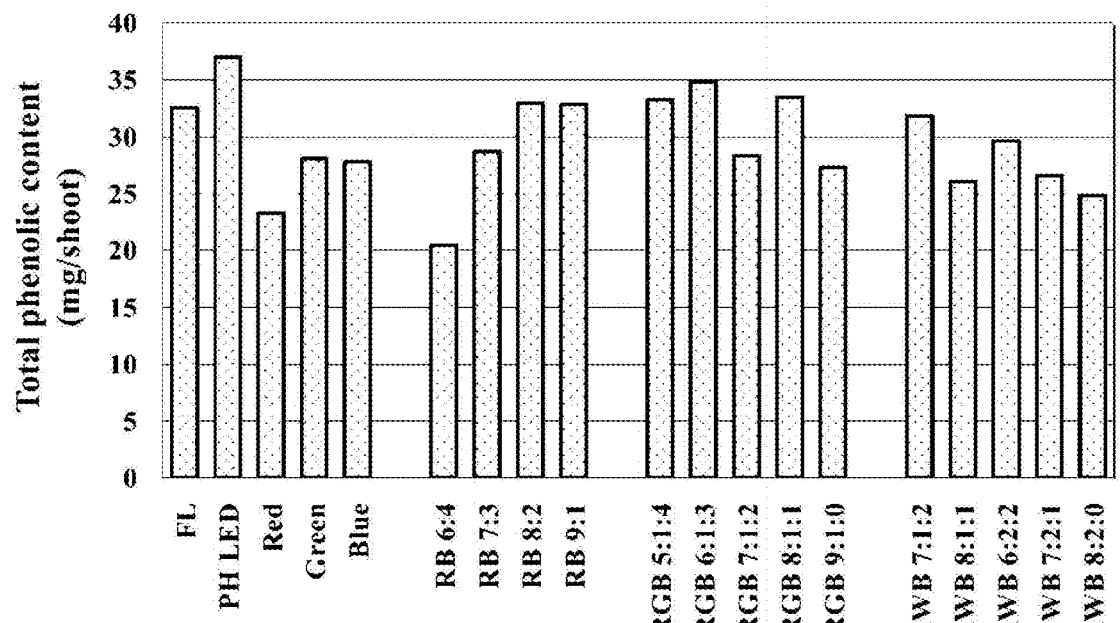
Figure 4D:
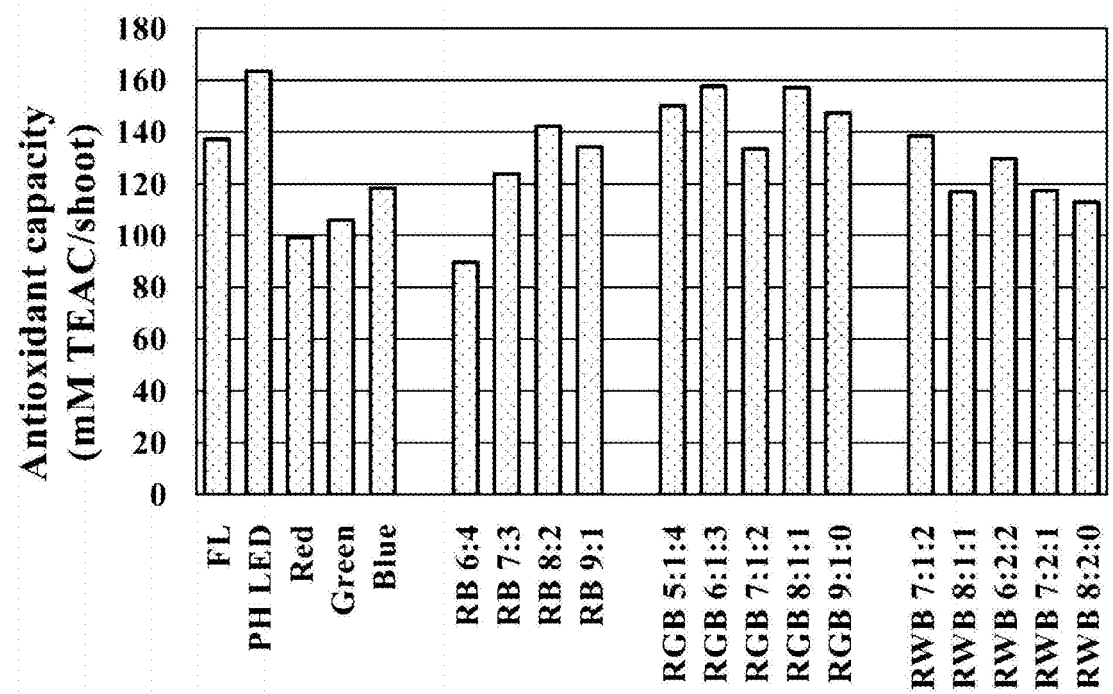

FIGS. 2A and 2B are graphs showing shoot fresh weight and shoot dry weight of the aerial part of *Crepidiastrum denticulatum*, respectively.

FIGS. 3A to 3D are graphs showing the number of leaves, leaf area, leaf length, and leaf width, respectively.

FIGS. 4A to 4D are graphs showing the total phenolic concentration, the antioxidant capacity, and the total phenolic content and the antioxidant capacity calculated per plant, respectively.

Figure 5A:
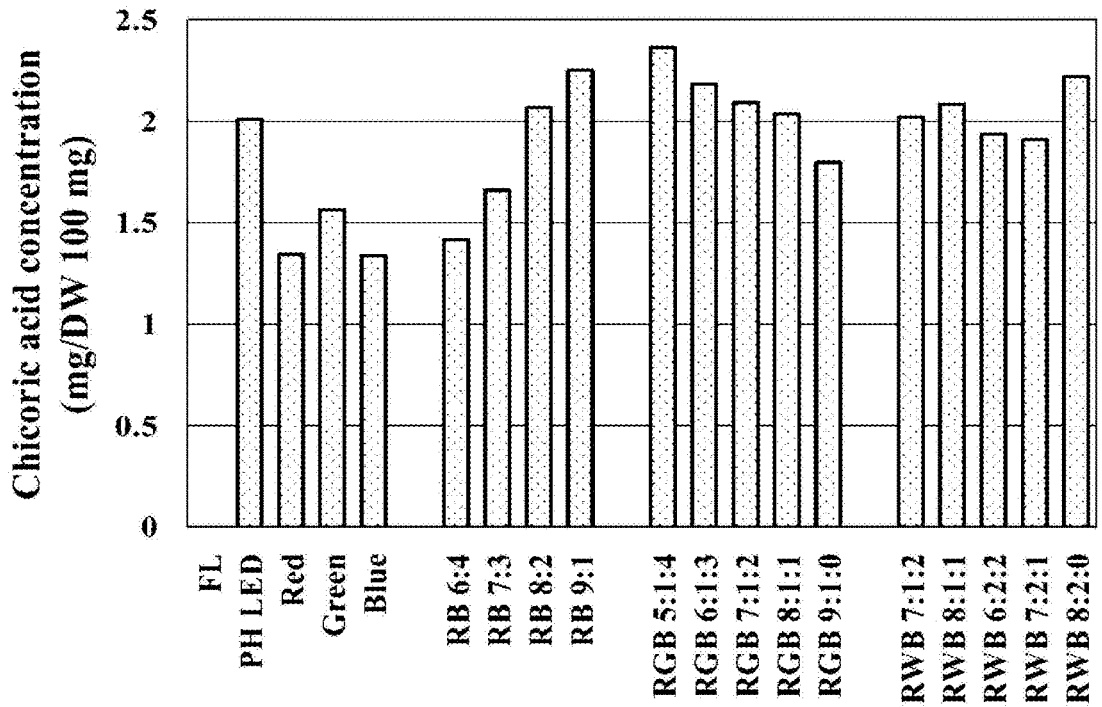
Figure 5B:
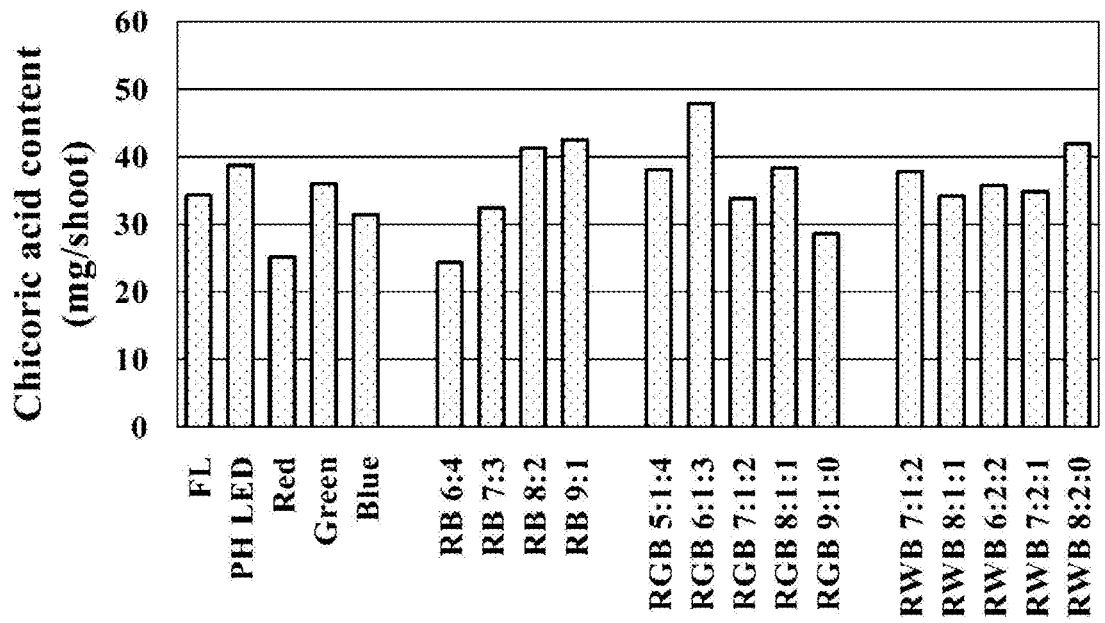
Figure 5D:
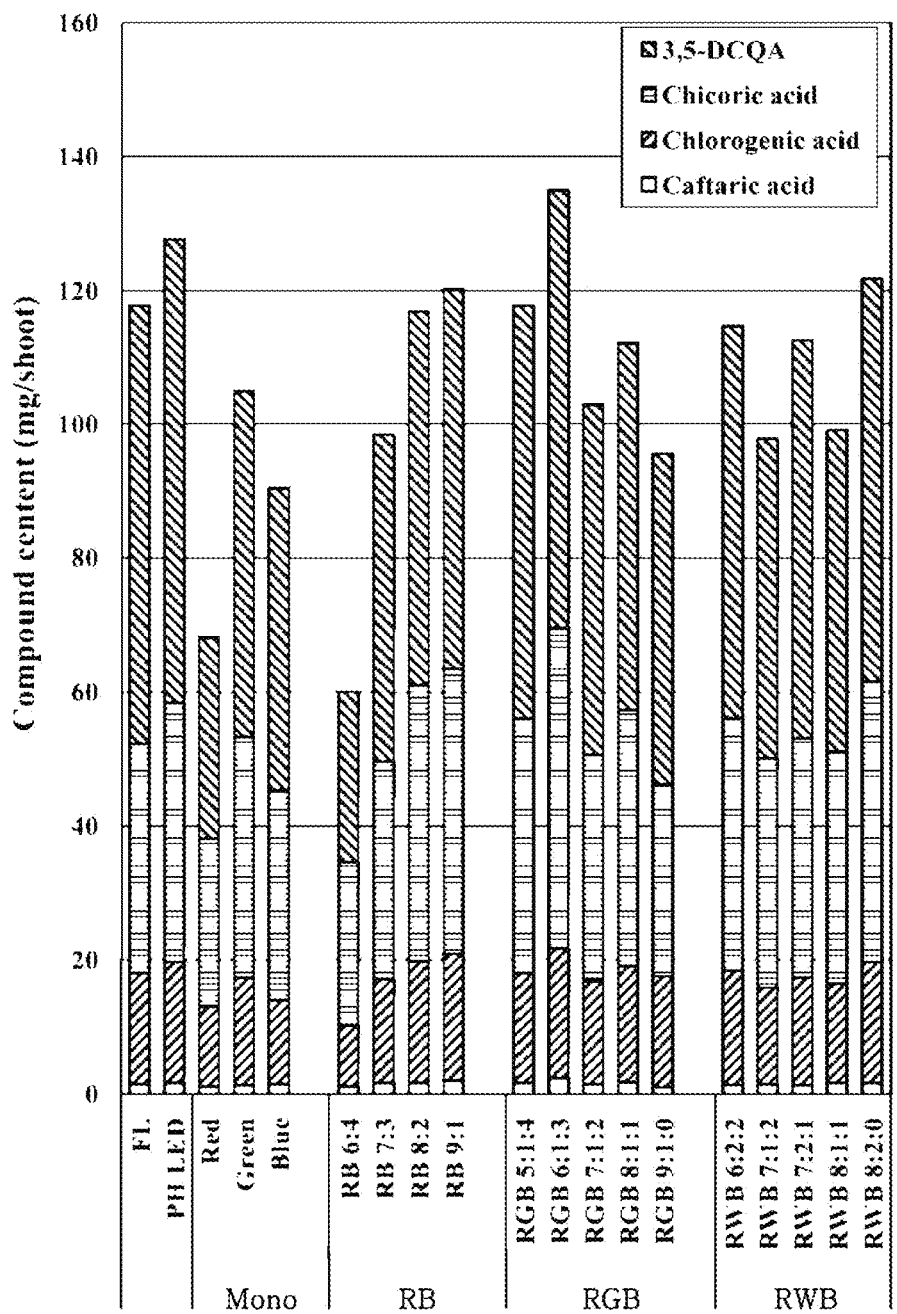

FIGS. 5A and 5B are graphs showing chicoric acid concentration, and chicoric acid content calculated per plant. FIGS. 5C and 5D are graphs showing the compound concentrations of caftaric acid, chlorogenic acid, chicoric acid, and 3,5-di-O-caffeoylquinic acid (3,5-DCQA) and the contents of thereof calculated per plant. As shown in the graphs, on the 6th week after the planting, the shoot fresh weight and the shoot dry weight of the aerial part increased in green light (Green) and blue light (Blue), among the monochromatic rays (shown as Mono in the drawings), and the shoot fresh weight and the shoot dry weight were the highest in the RGB 6:1:3 treatment group among the RGB mixed lights.

Further, the number of leaves was the highest in the RWB 6:2:2 treatment group. The leaf area was the highest in green light and blue light in monochromatic light, and was the highest in the RGB 6:1:3 treatment group among the RGB mixed lights, which were similar to the results of the shoot fresh weight and the shoot dry weight leaves of the aerial part.

Further, the total phenolic concentration and the antioxidant capacity were the highest in the fluorescent lamp (FL) group and the RGB 5:1:4 treatment group, and the total phenolic content and the antioxidant activity calculated per plant were generally high in the RGB treatment group.

Further, the content calculated per plant of the chicoric acid, which is the target substance among major bioactive substances of *Crepidiastrum denticulatum*, was the highest in the RGB 6:1:3 treatment group which showed good growth. Further, the total contents of chicoric acid, caftaric acid, chlorogenic acid, and 3,5-di-O-caffeoylquinic acid (3,5-DCQA), which are major bioactive substances, were the highest in the RGB 6:1:3 treatment group.

As such, the growth of the *Crepidiastrum denticulatum* and the chicoric acid content, which is the target substance, increased in the RGB 6:1:3 mixed light in the light quality treatments using mixed LEDs at various ratios. This technology may refer to that pharmaceutical-based plant raw materials may be capable of being mass-produced uniformly and stably in a plant factory, which is a closed plant production system.

<Example 2> Confirmation of Growth of *Crepidiastrum denticulatum* According to Far-Red LED In Example 2, the growth and the useful substances of *Crepidiastrum denticulatum* were confirmed using various far-red LEDs. The phytochrome of the plant body is converted from an inactive state to an active state by the red light (R), and is converted from the active state to the inactive state by the far-red light (FR). This conversion of phytochrome generates plant growth and morphological changes depending on the ratio of red light to far-red light (R/FR).

Figure 6:
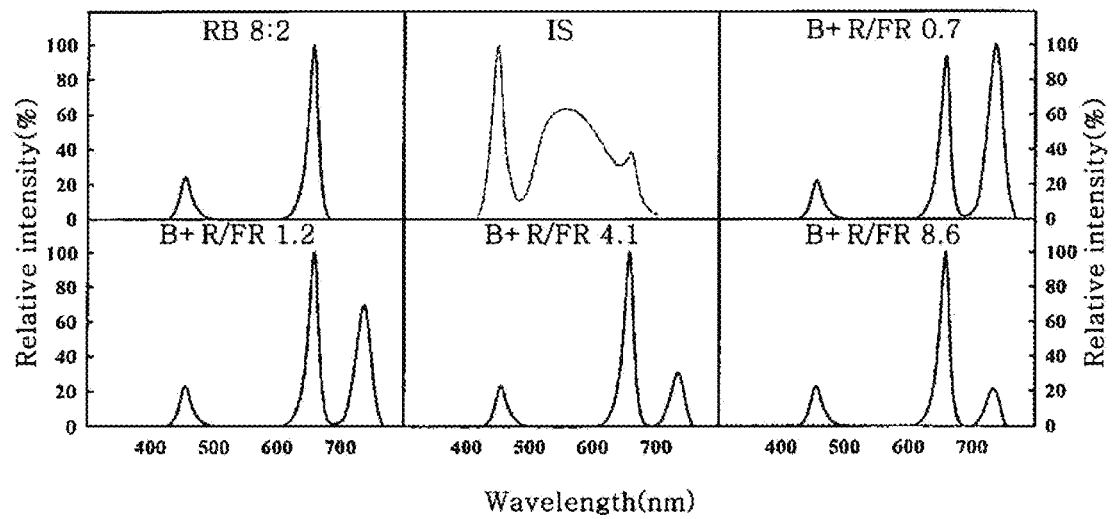
FIG. 6 is a graph showing far-red LEDs (RB 8:2 LED mixed light, lights obtained by adding a far-red LED to RB 8:2 LED mixed light which are adjusted in four kinds of R/FR ratios) according to an exemplary embodiment.
Figure 7A:
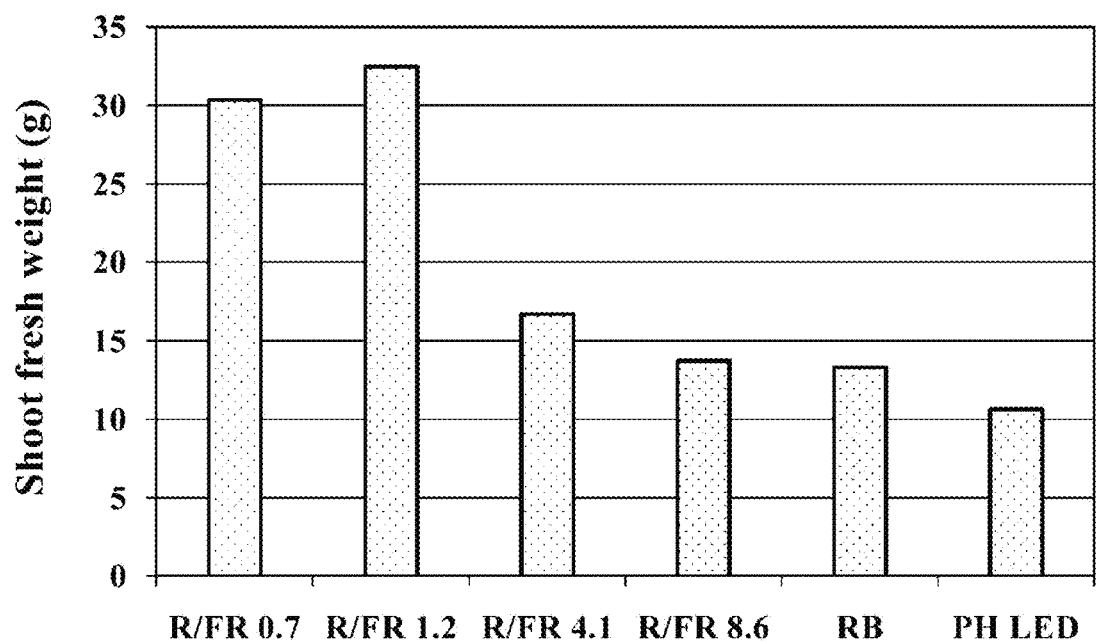
FIGS. 7A, 7B, 7C, 7D, 7E, and 7F are graphs showing results obtained by measuring the shoot fresh weight, the shoot dry weight, the leaf area, the leaf length, the leaf width, and the number of leaves of the aerial part of *Crepidiastrum denticulatum* which is treated with the far-red LED, respectively.
Figure 7B:
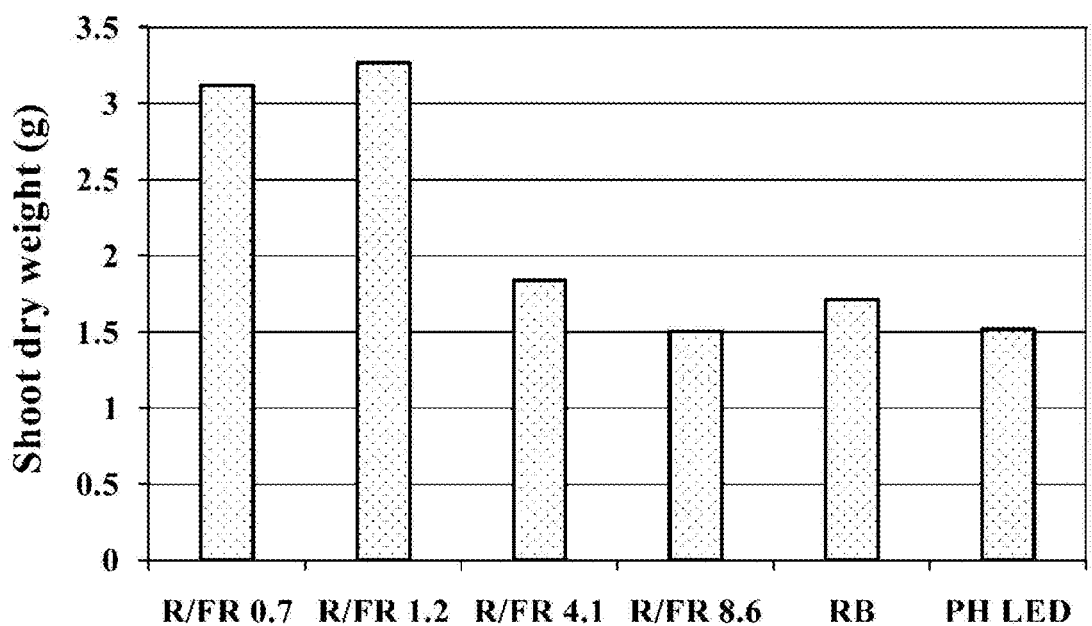
Figure 7C:
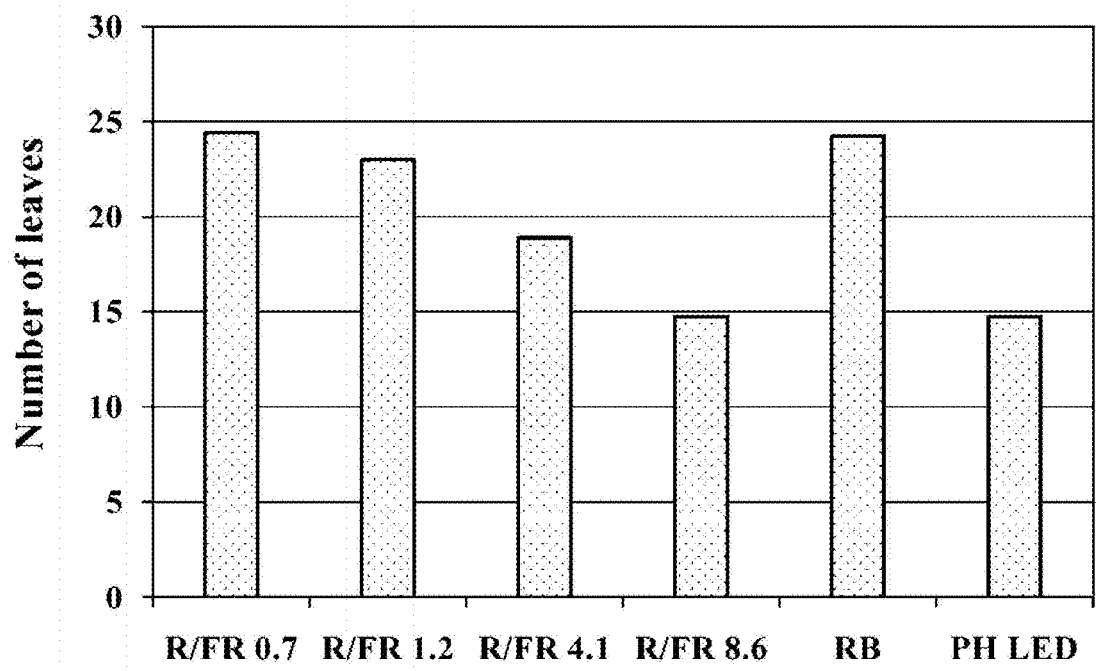
Figure 7D:
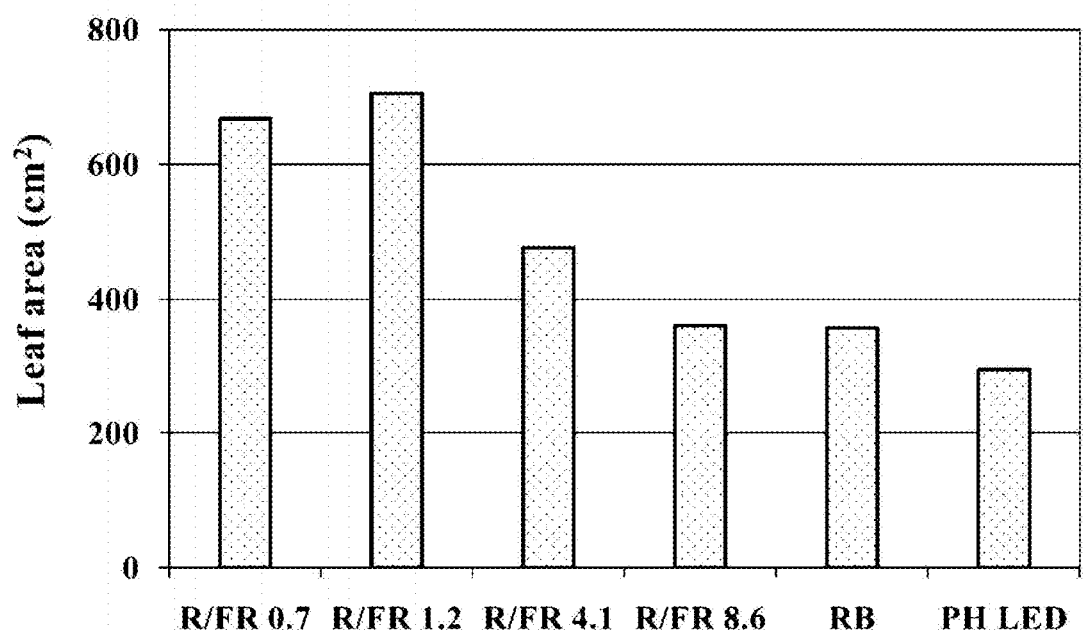
Figure 7E:
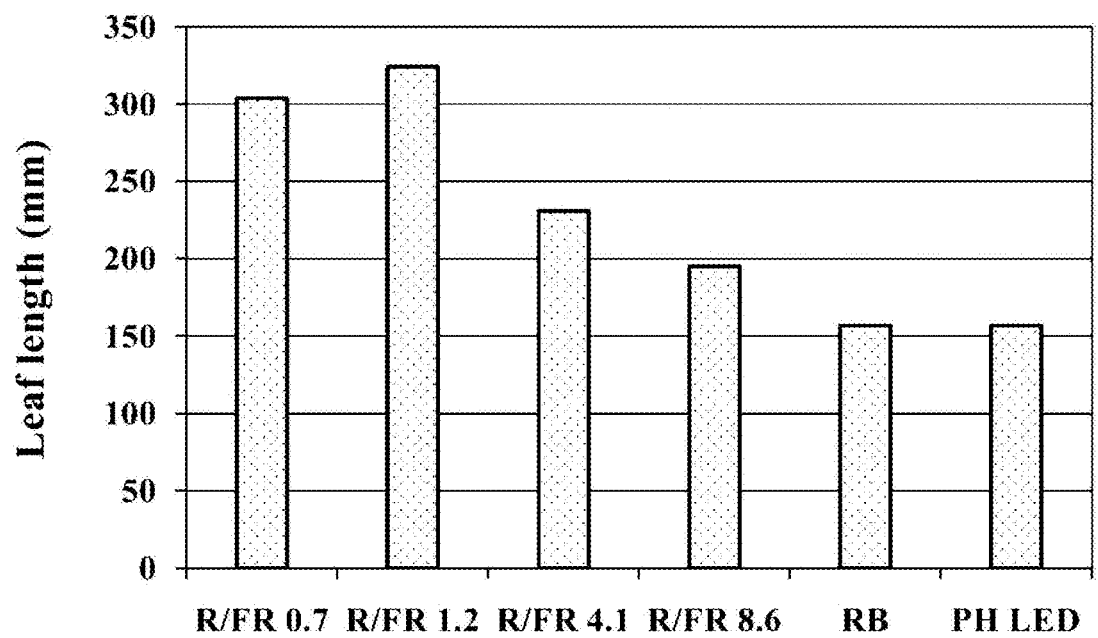
Figure 7F:
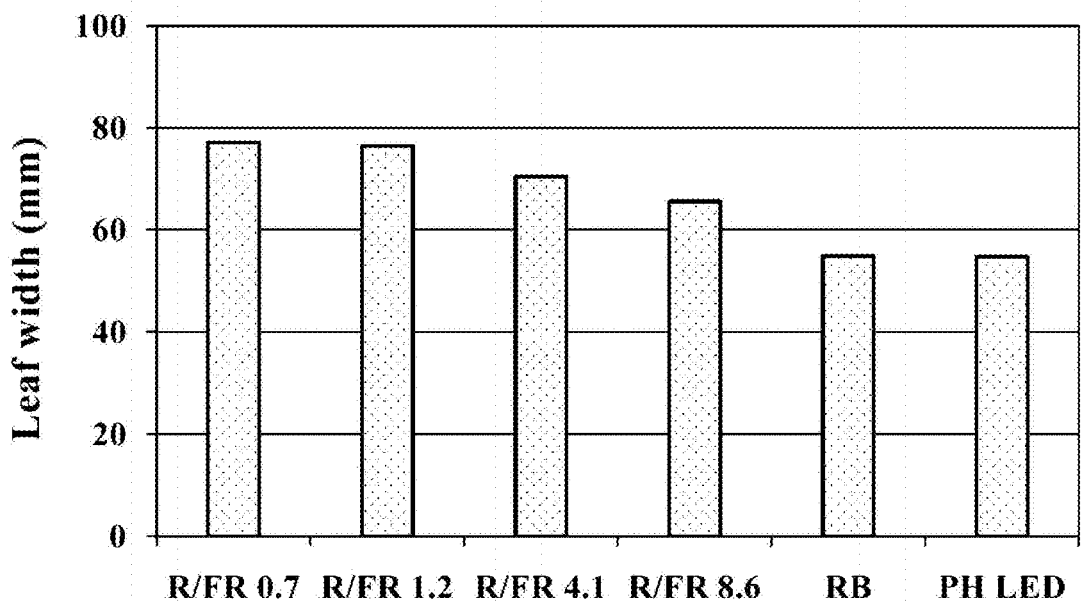
Figure 8A:
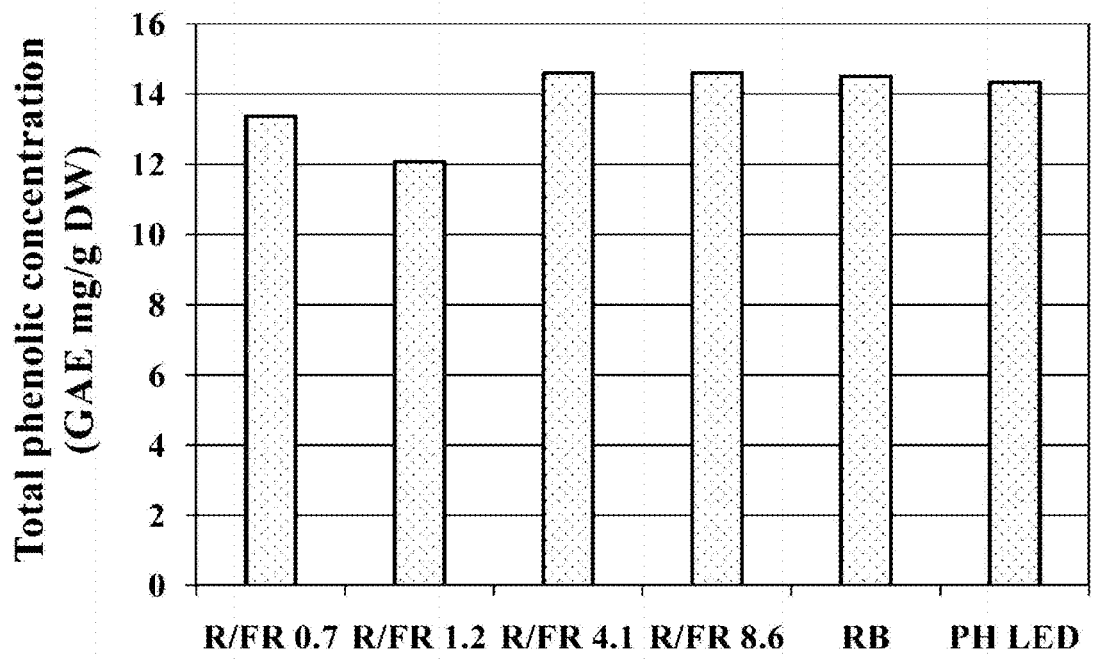
FIGS. 8A, 8B, 8C, and 8D are graphs showing results obtained by measuring antioxidation and total phenolic compound of *Crepidiastrum denticulatum* which is treated with the far-red LED, respectively.
Figure 8B:
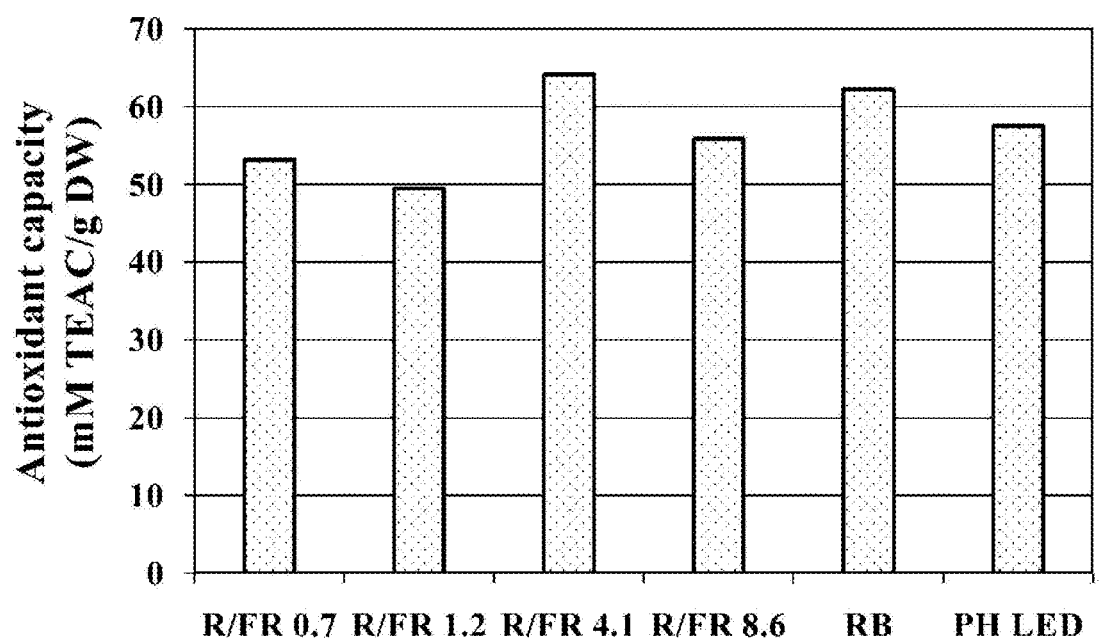
Figure 8C:
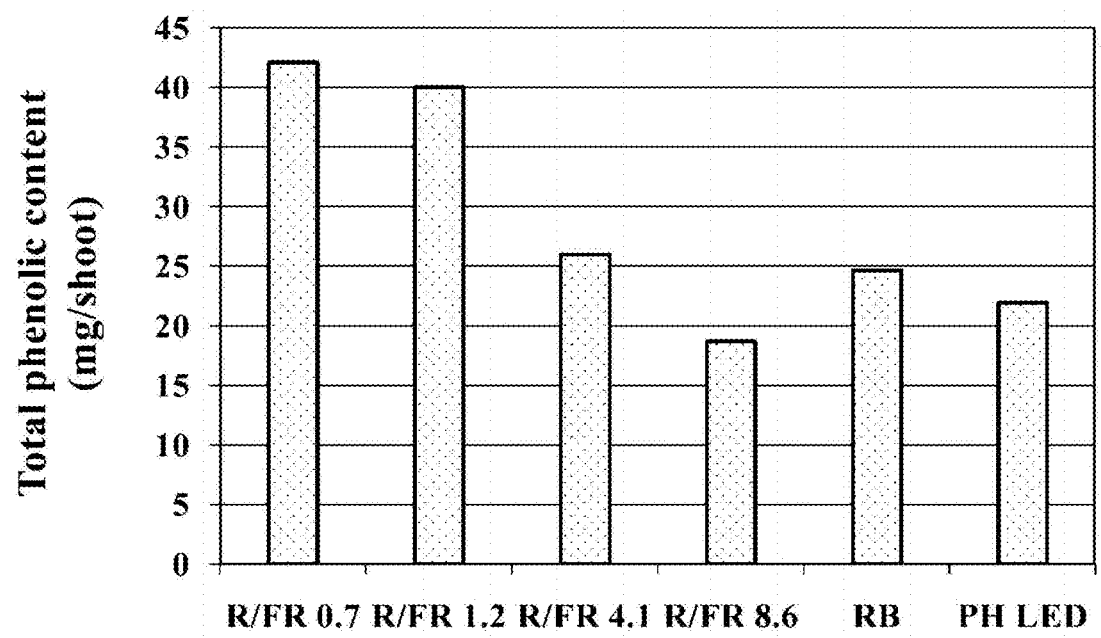
Figure 8D:
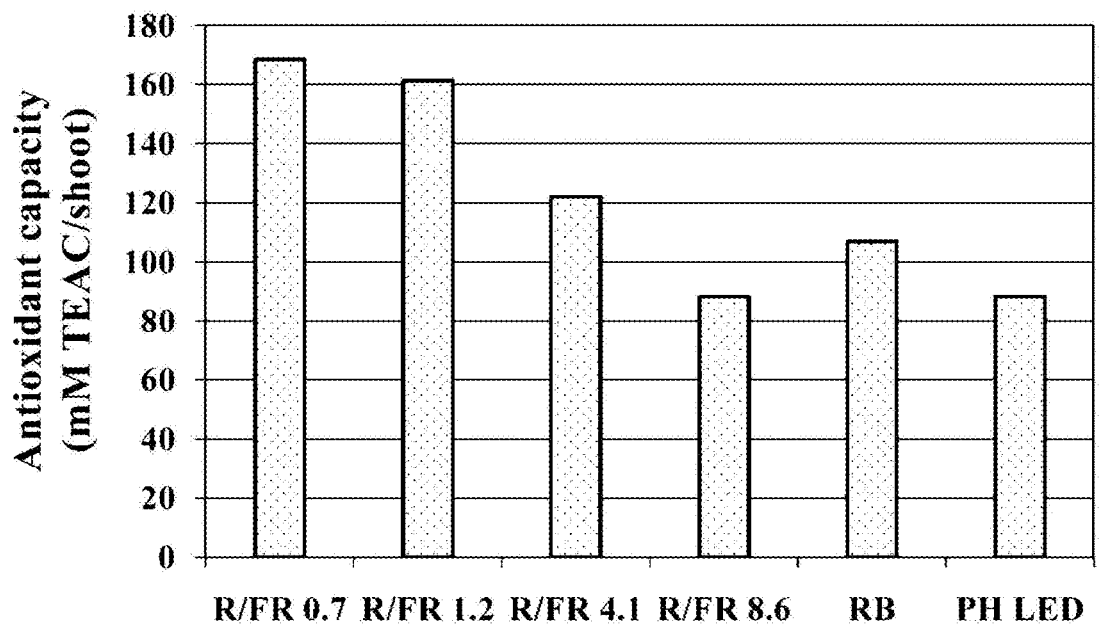
Figure 9A:
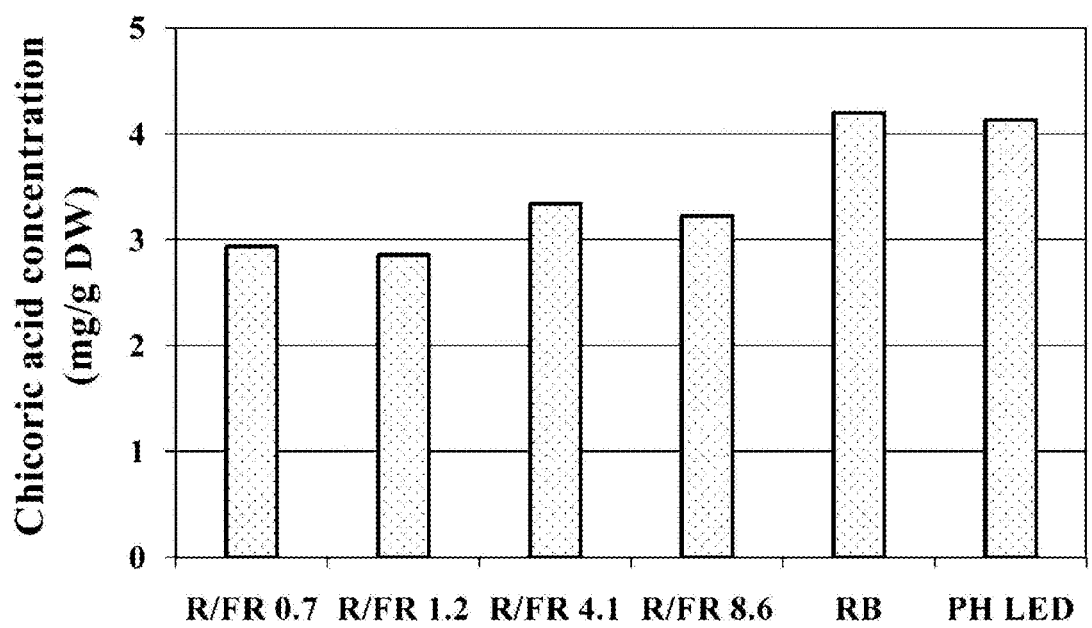
FIGS. 9A, 9B, 9C, 9D, 9E, and 9F are graphs showing results obtained by measuring chicoric acid and phenylpropanoid substance of *Crepidiastrum denticulatum* which is treated with the far-red LED, respectively.
Figure 9B:
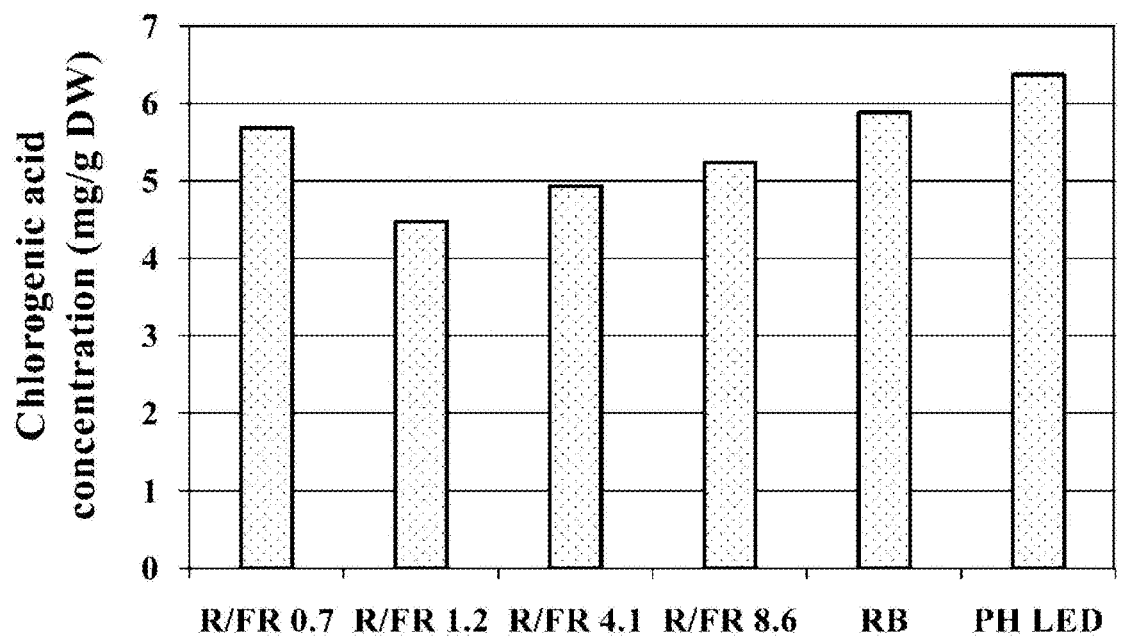
Figure 9C:
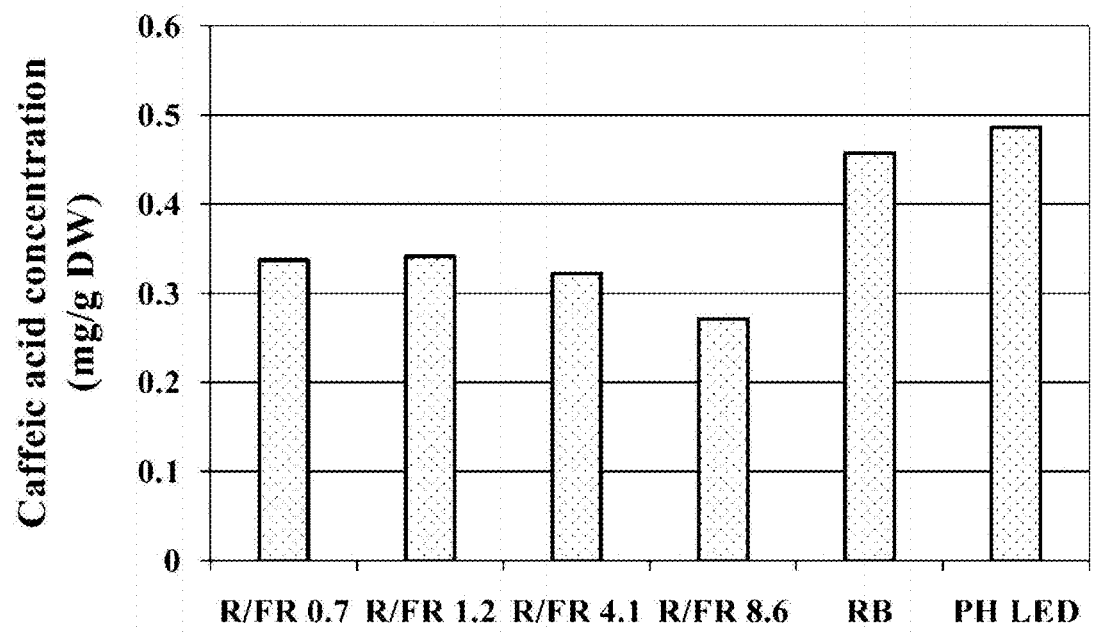
Figure 9D:
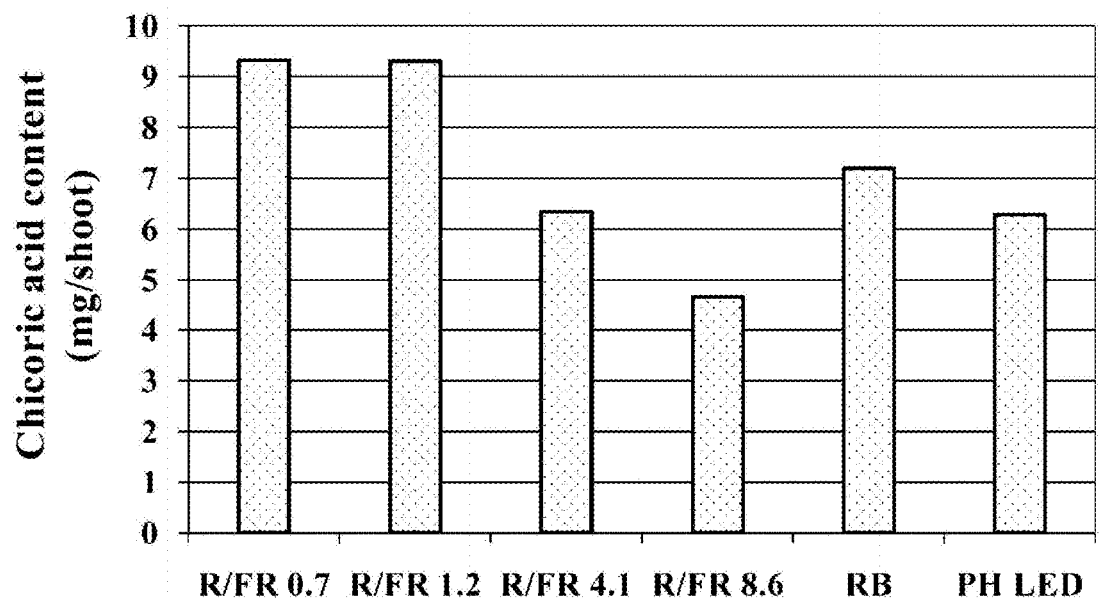
Figure 9E:
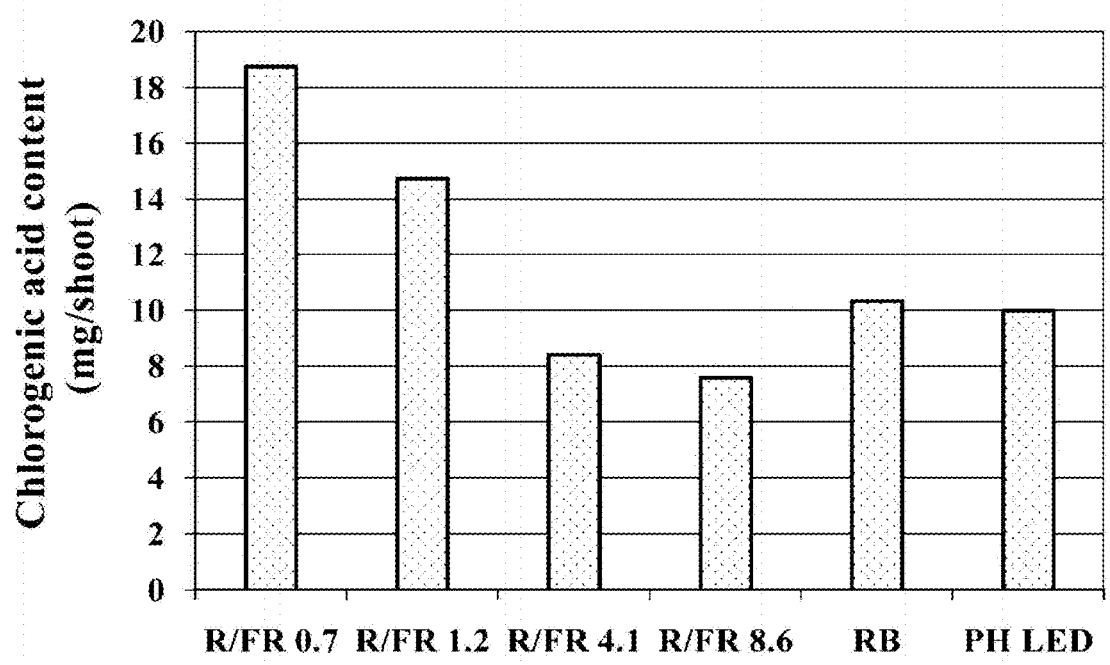
Figure 9F:
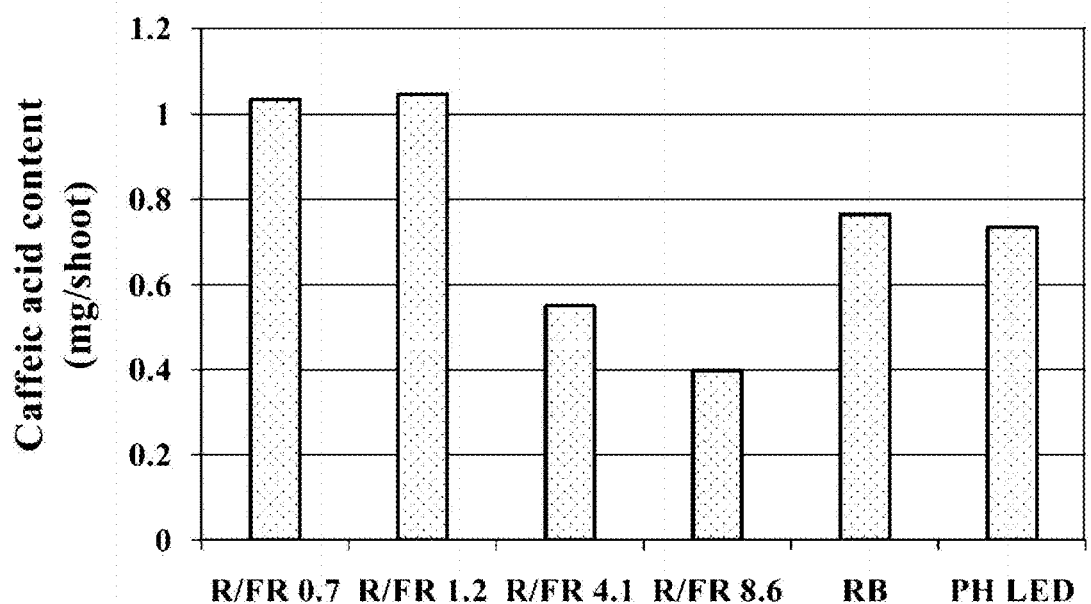
Figure 10A:
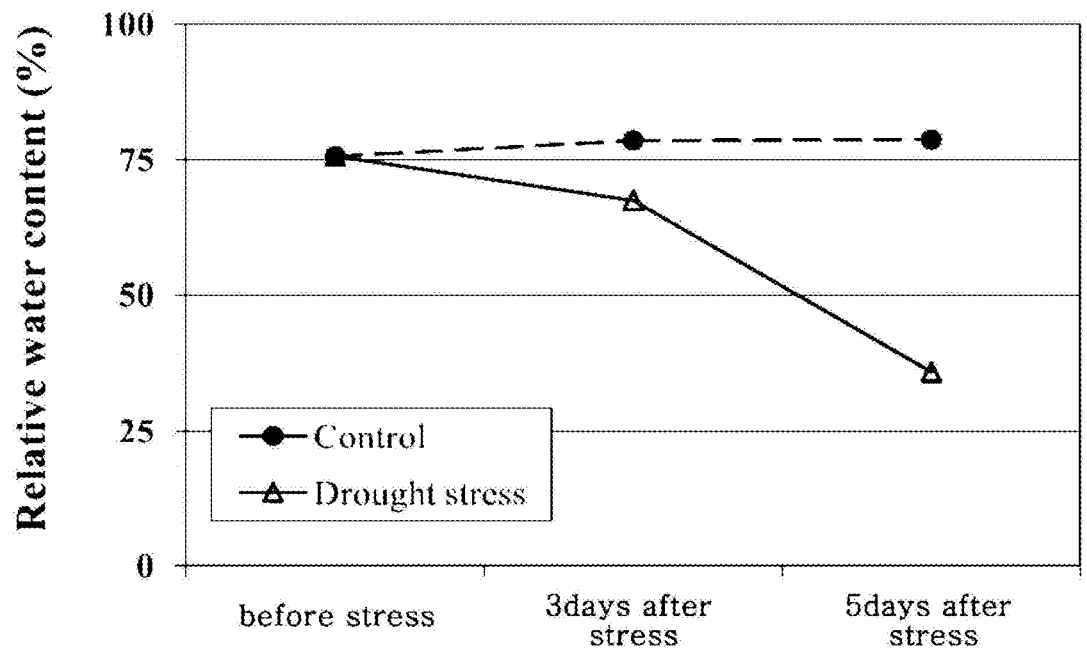
FIGS. 10A, 10B, 10C, and 10D are graphs showing results obtained by measuring the phenolic compound, chicoric acid, and antioxidation included in *Crepidiastrum denticulatum*, and water content of *Crepidiastrum denticulatum* leaf according to drying stress treatment, respectively.
Figure 10B:
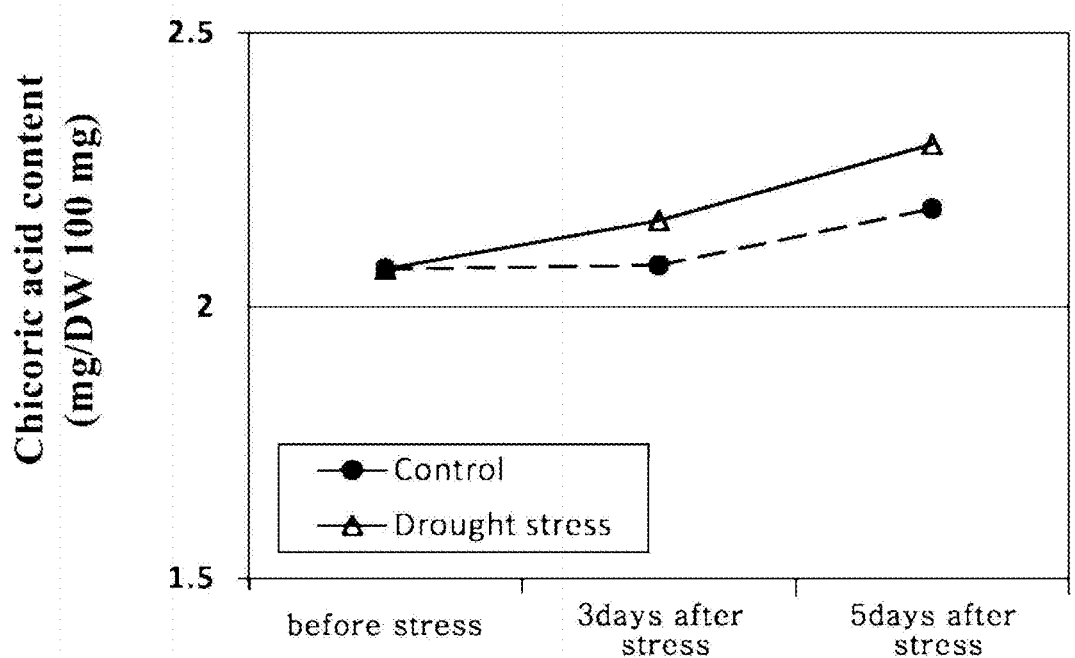
Figure 10C:
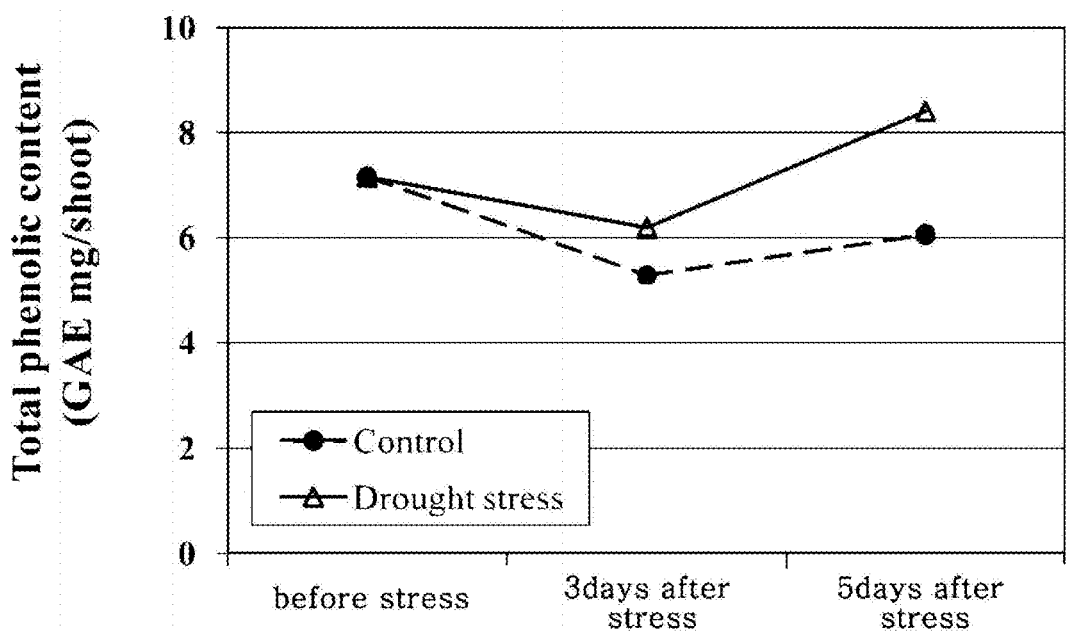
Figure 10D:
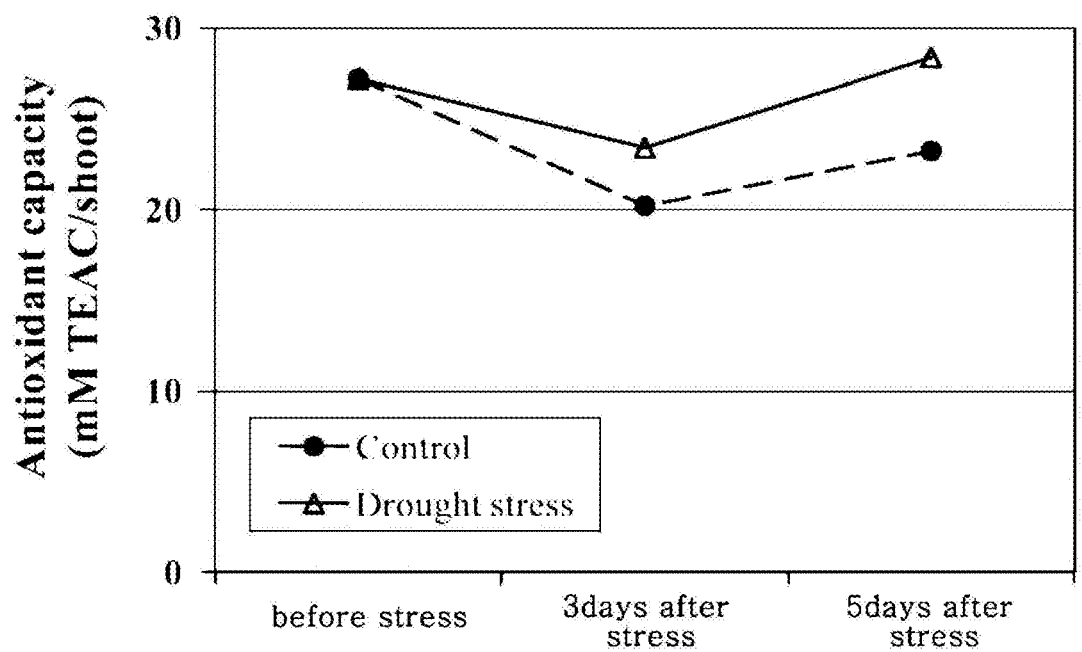

According to exemplary embodiments, four R/FR ratios were adjusted by adding a far-red (FR) LED in the same light intensity (PPFD), which is 130 µmol/m$^2$/s, of the RB 8:2 mixed LED, as shown in FIG. 6. *Crepidiastrum denticulatum* were cultivated for 6 weeks after planting in a closed plant production system under an environment with a temperature of 20° C., a carbon dioxide concentration of 1000 ppm, and a relative humidity of 60% in light to which the far-red LED was added to the RB 8:2 mixed LED, and in light to which the far-red LED was not added to the RB 8:2 mixed LED.

On the 6th week after the planting, the shoot fresh weight, the shoot dry weight, the leaf area, the leaf length, the leaf width, and the number of leaves of the aerial part for each light source were measured. In addition, the concentrations, contents and antioxidant activities of the total phenolic compound, chicoric acid, chlorogenic acid, and caffeic acid were also analyzed.

FIGS. 7A to 7D are graphs showing the shoot fresh weight, the shoot dry weight, the number of leaves, the leaf area, the leaf length, and the leaf width of the aerial part, respectively.

FIGS. 8A to 8D are graphs showing the total phenolic compound, antioxidant capacity, and the total phenolic content and the antioxidant capacity calculated per plant, respectively.

FIGS. 9A to 9F are graphs showing concentrations and contents calculated per plant of chicoric acid, chlorogenic acid, and caftaric acid, respectively.

As shown in the graphs, the shoot fresh weight, the shoot dry weight, the leaf area, the leaf length, and the leaf width of the aerial part were significantly higher in R/FR 0.7 and 1.2 treatment groups, in which the R/FR ratio was low, i.e., the ratio of far-red LED was high, as compared to control group without the far-red LED and the commercial light source (IS). In particular, the R/FR 1.2 treatment group showing the best growth, did not show a significant difference in the number of leaves as compared to the control group, but the shoot fresh weight increased 2.4 times and the shoot dry weight increased 1.9 times, and the leaf length and leaf width increased greatly, thus resulting in an increase in leaf area. Further, since the total phenolic concentration per unit shoot dry weight of the aerial part of *Crepidiastrum denticulatum* did not show a significant difference in all treatment groups, the total phenolic content was the highest in the R/FR 0.7 and 1.2 treatment groups showing remarkably good growth in the aerial part, and the antioxidant capacity also showed a similar tendency.

Further, the concentrations of chicoric acid, chlorogenic acid and caffeic acid, which are major bioactive substances, tended to decrease slightly in the R/FR 0.7 and 1.2 treatment groups which had low R/FR ratios, as compared to the control group, but the content capable of being produced from one plant body of *Crepidiastrum denticulatum* were higher in the R/FR 0.7 and 1.2 treatment groups.

Accordingly, exemplary embodiments provide an appropriate R/FR ratio which increases the growth of *Crepidiastrum denticulatum*, which is a medicinal plant and promotes the functional substance content, thereby promoting the production of *Crepidiastrum denticulatum* with high quality in the closed plant production system.

<Example 3> Analysis of Bioactive Substances of *Crepidiastrum denticulatum* by Drying Stress In order to confirm the bioactive substances of *Crepidiastrum denticulatum* using drying environment stress, *Crepidiastrum denticulatum* was cultivated for 5 weeks after being planted in a closed plant growth system under conditions of a temperature of 20° C., a humidity of 60%, and 150 μmol/m$^2$/s PPFD. On the 5th week after planting *Crepidiastrum denticulatum*, watering was stopped, and *Crepidiastrum denticulatum* was treated with drying stress for 5 days. Then, the total phenolic content, antioxidant capacity, and the chicoric acid content were analyzed.

FIGS. 10A to 10D are graphs showing the relative water content of leaves, the chicoric acid content, and the total phenolic content and the antioxidant capacity calculated per plant, respectively. In FIGS. 10A to 10D, Control is a control group which is *Crepidiastrum denticulatum* without stress treatment, and Drought stress is *Crepidiastrum denticulatum* which is treated with drying stress.

As shown in the graphs, the relative water content of leaves significantly decreased by drying stress treatment, and the content of chicoric acid, which is the bioactive substance, increased as compared with the control group. In addition, the total phenolic content and the antioxidant capacity per plant increased as compared with the control group at the 3rd day and the 5th day after the drying treatment.

<Example 4> Analysis of Bioactive Substances of *Crepidiastrum denticulatum* by Drying Stress with Two Conditions In order to confirm the bioactive substances of *Crepidiastrum denticulatum* using drying environment stress with two conditions, *Crepidiastrum denticulatum* was cultivated for 5 weeks after being planted in a closed plant production system under conditions of a temperature of 20° C., a humidity of 60%, a carbon dioxide concentration of 1000 ppm, and 300 μmol/m$^2$/s PPFD. On the 5th week after planting, *Crepidiastrum denticulatum* was treated with two ways drying stress (e.g., exposing a wick to about 3 cm, and complete stop of watering), respectively, and the total phenolic content, the chicoric acid content, and the leaf water potential were analyzed on the 6th week after the planting.

FIG. 11A is a graph showing the leaf water potential, and FIGS. 11B and 11C are graphs showing the total phenolic content and the chicoric acid content calculated per plant. In FIGS. 11A to 11C, Control is a control group, Drought stress 1 is *Crepidiastrum denticulatum* treated with drying stress using one wick, and Drought stress 2 is *Crepidiastrum denticulatum* treated with drying stress using complete stop of watering.

As shown in the graphs, in the treatment group in which the watering is completely stopped, the leaf water potential drastically decreased on the 2nd day after drying treatment as compared to the control group. In addition, the drying stress with two conditions increased the total phenolic content and the chicoric acid content per plant.

<Example 5> Analysis of Bioactive Substances of *Crepidiastrum denticulatum* by Composite Low Temperature Stress In order to confirm the bioactive substances of *Crepidiastrum denticulatum* using composite low temperature environment stress, *Crepidiastrum denticulatum* was cultivated for 5 weeks after being planted in a closed plant production system under conditions of a temperature of 20° C., a humidity of 60%, a carbon dioxide concentration of 1000 ppm, and 300 μmol/m$^2$/s PPFD. Thereafter, *Crepidiastrum denticulatum* was treated with four kinds of composite low temperature stress (light intensity 300 μmol/m$^2$/s+low temperature 10° C., light intensity 150 μmol/m$^2$/s+low temperature 10° C., 20° C. during the day+10° C. during the night, 10° C. during the day+20° C. during the night). The functional substance was analyzed on the 6th week after planting.

Figure 12A:
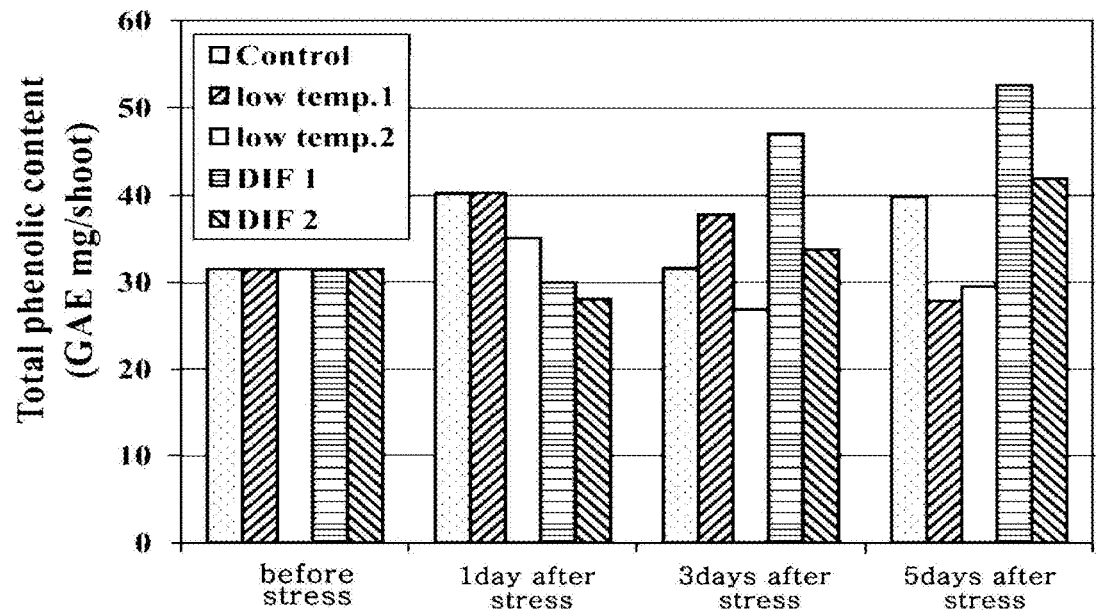
FIGS. 12A and 12B are graphs showing results obtained by measuring the total phenolic compound and chicory acid included in *Crepidiastrum denticulatum* according to composite cold stress treatment (light intensity 300 $\mu mol/m^2/s$+ low temperature 10° C. 150 $\mu mol/m^2/s$+low temperature 10° C., 20° C. during the day+10° C. during the night, 10° C. during the day+20° C. during the night), respectively.
Figure 12B:
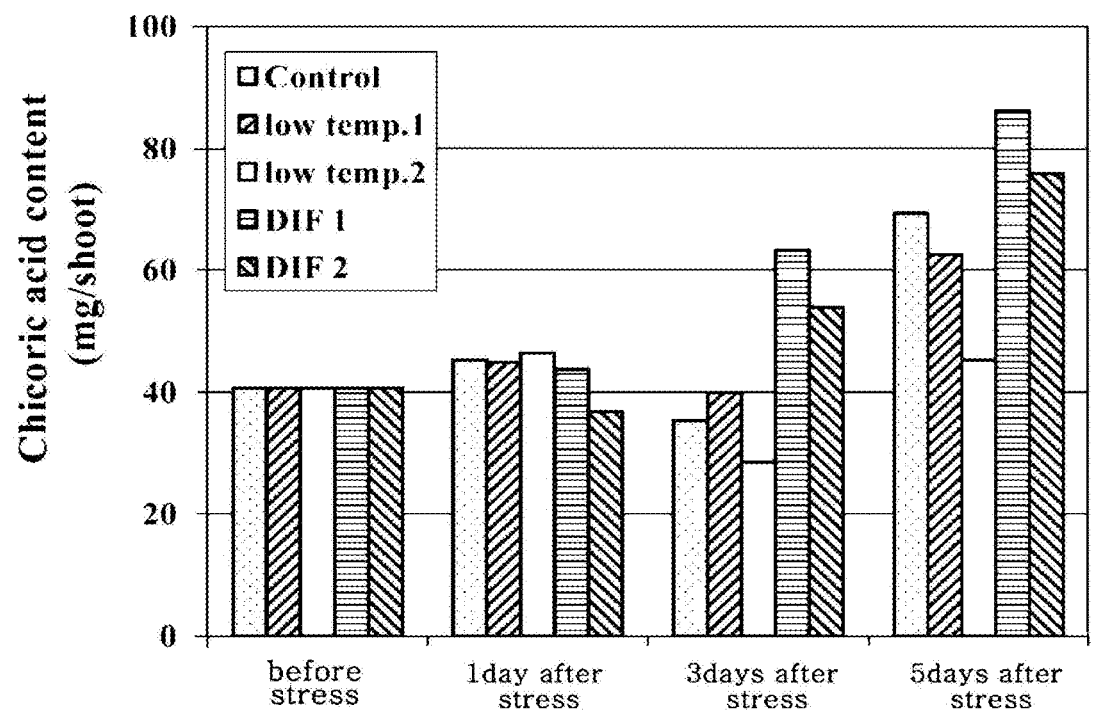

FIGS. 12A and 12B are graphs showing the total phenolic content and the chicoric acid content calculated per plant, respectively. In FIGS. 12A and 12B, Control refers to a control group, low temp. 1 is *Crepidiastrum denticulatum* stress-treated with a light intensity 300 μmol/m$^2$/s+low temperature of 10° C., low temp. 2 is *Crepidiastrum denticulatum* stress-treated with a light intensity 150 μmol/m$^2$/ s+low temperature of 10° C., DIF 1 is *Crepidiastrum denticulatum* stress-treated with 20° C. during the day+10° C. during the night, and DIF 2 is *Crepidiastrum denticulatum* stress-treated with 10° C. during the day+20° C. during the night.

As shown in the drawings, the total phenolic content by the 4 ways of low-temperature stress treatment were the highest in the treatment group at low temperature 10° C. during the night on the 3rd day and the 5th day after treatment, as compared to other treatment groups including the control group. Further, the chicoric acid content was the highest in the treatment group with low temperature at 10° C. during the night and in the treatment group with low temperature at 10° C. during the day on the 3rd day and the 5th day after treatment.

<Example 6> Analysis of Bioactive Substances of *Crepidiastrum denticulatum* by UV-A LED

*Crepidiastrum denticulatum* was cultivated for 5 weeks after being planted in a closed plant production system under conditions of a temperature of 20° C., a humidity of 60%, a carbon dioxide concentration of 1000 ppm, and 300 μmol/m$^2$/s PPFD. Then, in order to confirm the bioactive substances of *Crepidiastrum denticulatum* using UV-A LED environmental stress, UV-A LED (370 nm or 385 nm wavelength) as an auxiliary light source was continuously irradiated on *Crepidiastrum denticulatum* for 1 week.

The functional substances were analyzed on the 6th week after planting *Crepidiastrum denticulatum*.

Figure 13A:
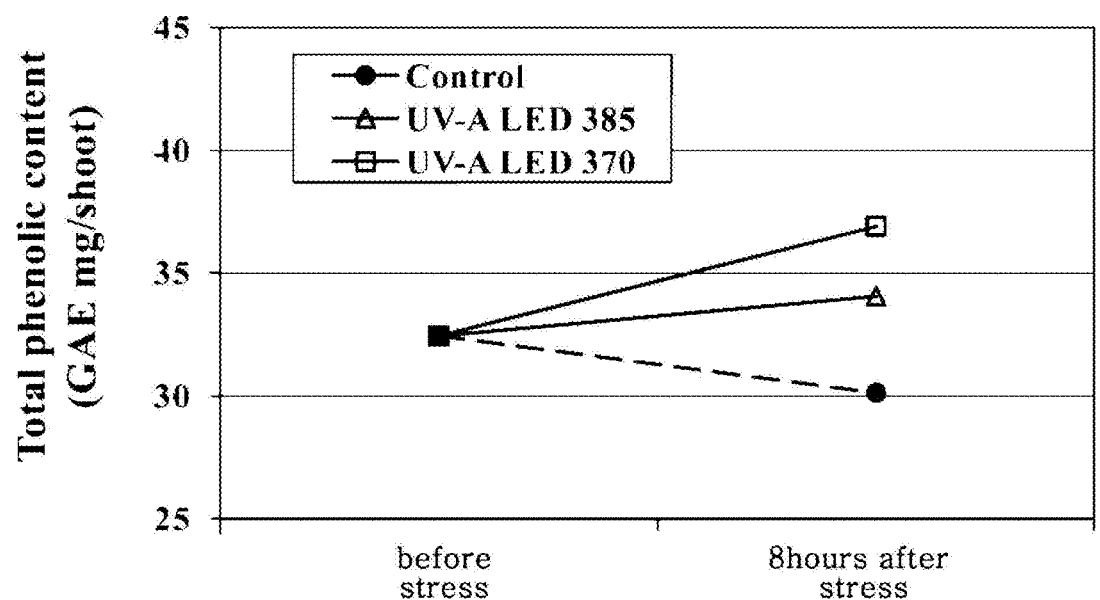
FIGS. 13A and 13B are graphs showing results obtained by measuring the total phenolic compound and chicory acid included in *Crepidiastrum denticulatum* according to UV-A LED assistant light source treatment, respectively.
Figure 13B:
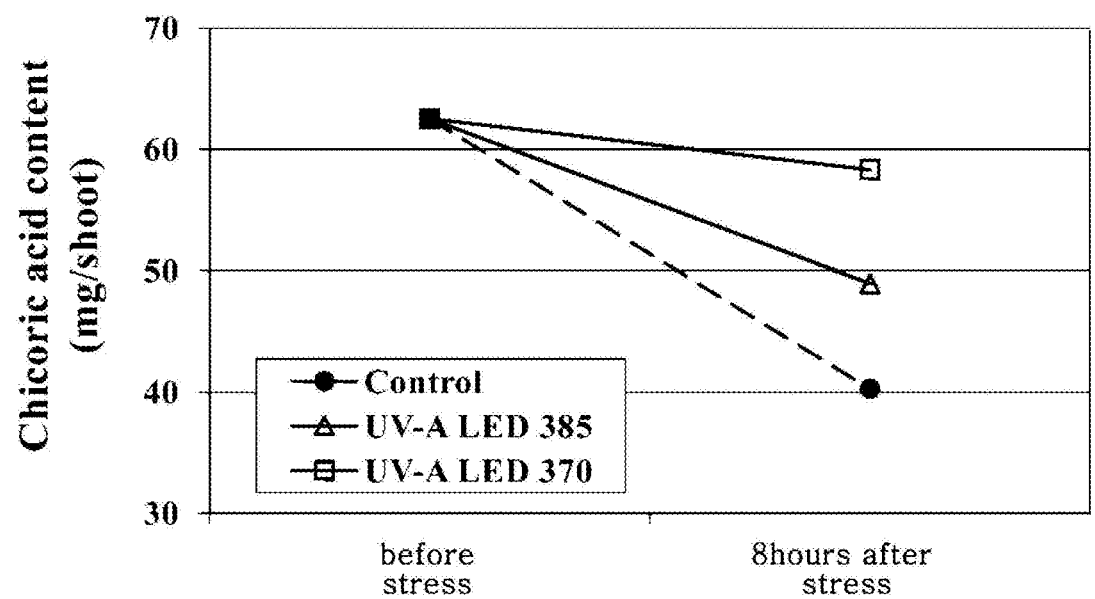
Figure 14A:
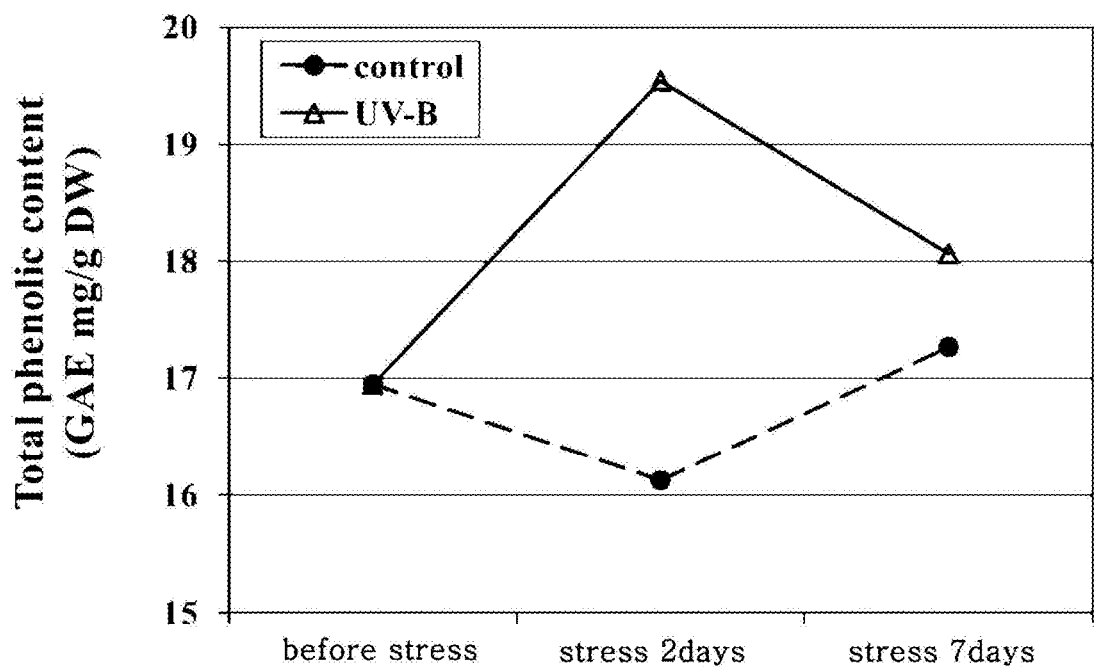
FIGS. 14A, 14B, 14C, and 14D are graphs showing results obtained by measuring the total phenolic compound, antioxidation, chicory acid, and 3,5-DCQA included in *Crepidiastrum denticulatum* according to UV-A LED assistant light source treatment, respectively.
Figure 14B:
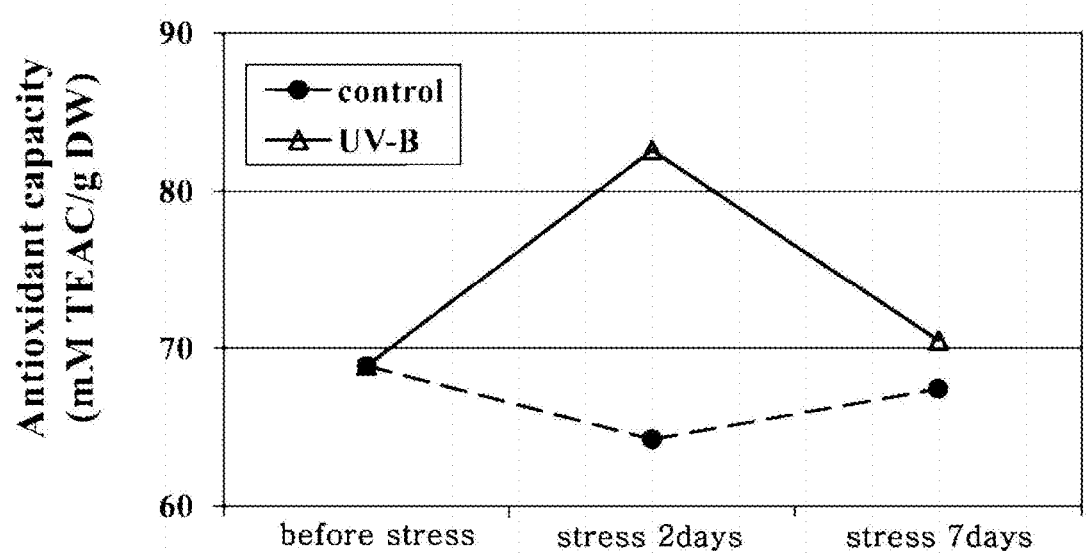
Figure 14C:
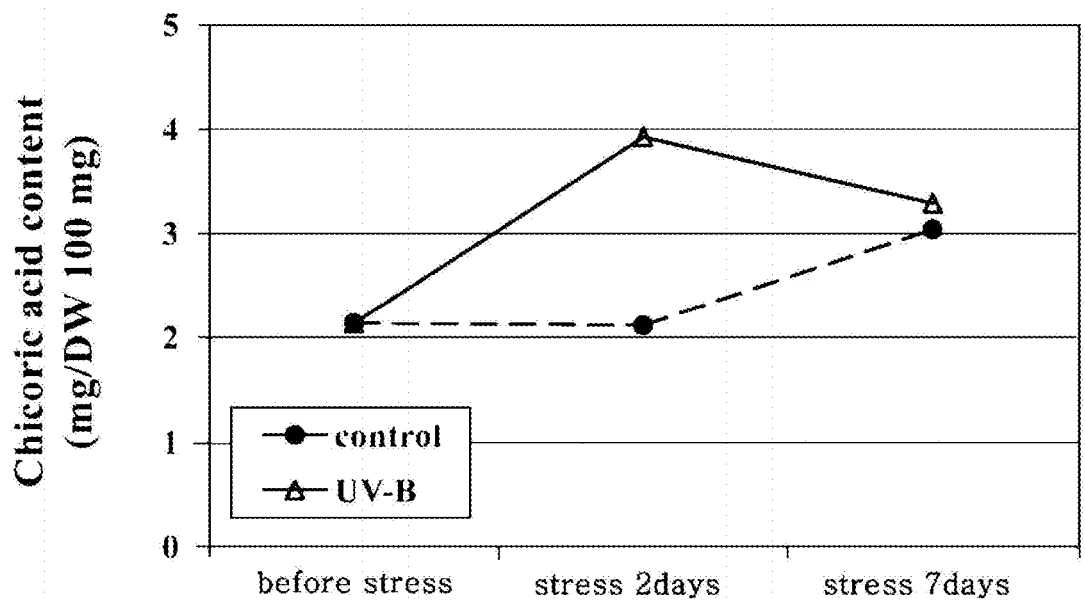
Figure 14D:
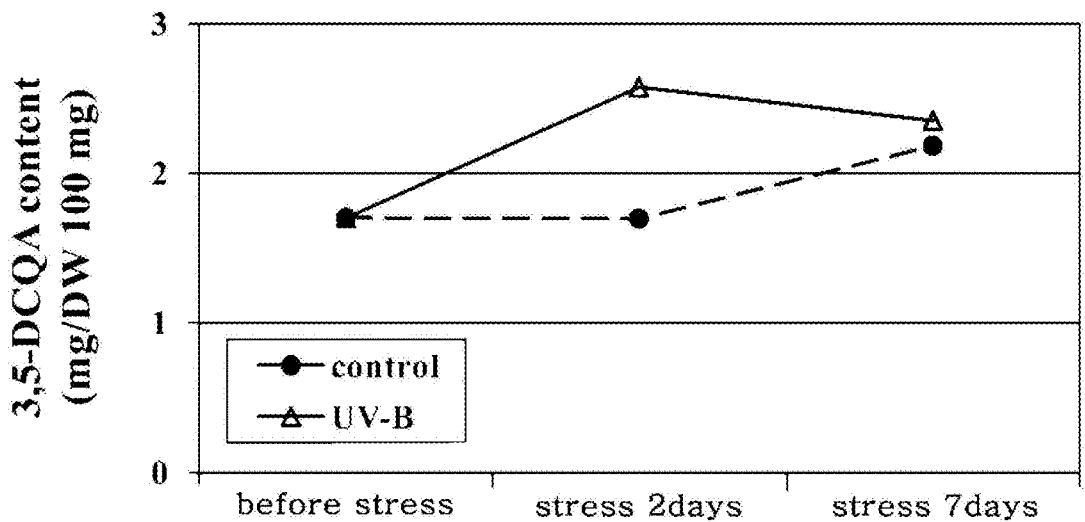

FIGS. 13A and 13B are graphs showing the total phenolic content and the chicoric acid content calculated per plant, respectively. In FIGS. 13A and 13B, Control is a control group. As shown in the graphs, upon reviewing after 8 hours of treatment with UV-A LED at a wavelength of 370 nm, the total phenolic content and the chicoric acid content were higher than those of the control group.

<Example 7> Analysis of Bioactive Substances of *Crepidiastrum denticulatum* by UV-B LED

*Crepidiastrum denticulatum* was cultivated for 6 weeks after being planted in a closed plant production system under conditions of a temperature of 20° C., a humidity of 60%, a carbon dioxide concentration of 1000 ppm, and 300 μmol/m$^2$/s PPFD. Then, in order to confirm the bioactive substances of *Crepidiastrum denticulatum* using the UV-B LED environmental stress, UV-B LED at a wavelength of 306 nm as an auxiliary light source was irradiated twice a day for 1 hour in every 11 hours during 1 week period.

The functional substances were analyzed on the 2nd day and the 7th day after the treatment. The total phenolic content, the antioxidant capacity, the chicoric acid content, and the 3,5-DCQA content were analyzed.

FIGS. 14A to 14D are graphs showing the total phenolic content, the antioxidant capacity, the chicoric acid content, and the 3,5-DCQA content, respectively. In FIGS. 14A to 14D, Control refers to a control group.

As shown in the graphs, the total phenolic content, the antioxidant capacity, the chicoric acid content, and 3,5-DCQA content of the UV-B treatment group increased and were higher than those of the control group on the 2nd day after the treatment.

The UV-B LED had an electric power of 13.34 W/m$^2$ per unit area and a cumulative energy up to the 2nd day of 40.02 W/m$^2$.

<Example 8> Analysis of Bioactive Substances of *Crepidiastrum denticulatum* by Chemical Elicitor In order to confirm the bioactive substances of *Crepidiastrum denticulatum* treated with a salicylic acid as a chemical elicitor, *Crepidiastrum denticulatum* was cultivated for 6 weeks after being planted in a closed plant production system under conditions of a temperature of 20° C., a humidity of 60%, a carbon dioxide concentration of 1000 ppm, and 300 μmol/m$^2$/s PPFD. Then, two concentrations of salicylic acid (1 mM or 2 mM) were evenly sprayed thereon twice a week. The functional substances were analyzed on the 7th week after being planted.

Figure 15A:
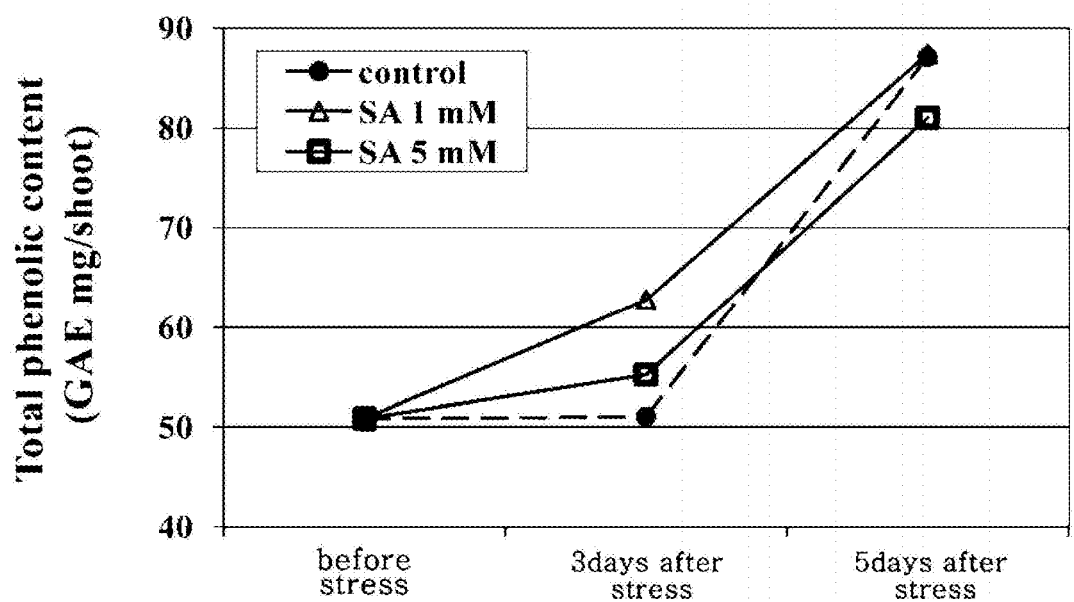
FIGS. 15A, 15B, and 15C are graphs showing results obtained by measuring the total phenolic compound, antioxidation, and chicory acid included in *Crepidiastrum denticulatum* according to salicylic acid treatment, respectively.
Figure 15B:
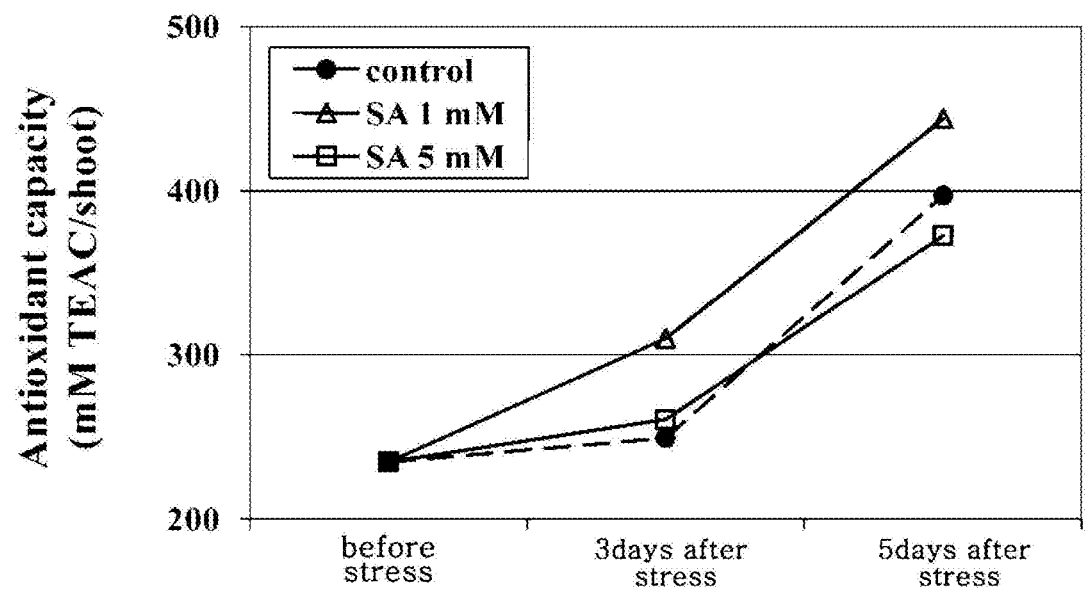
Figure 15C:
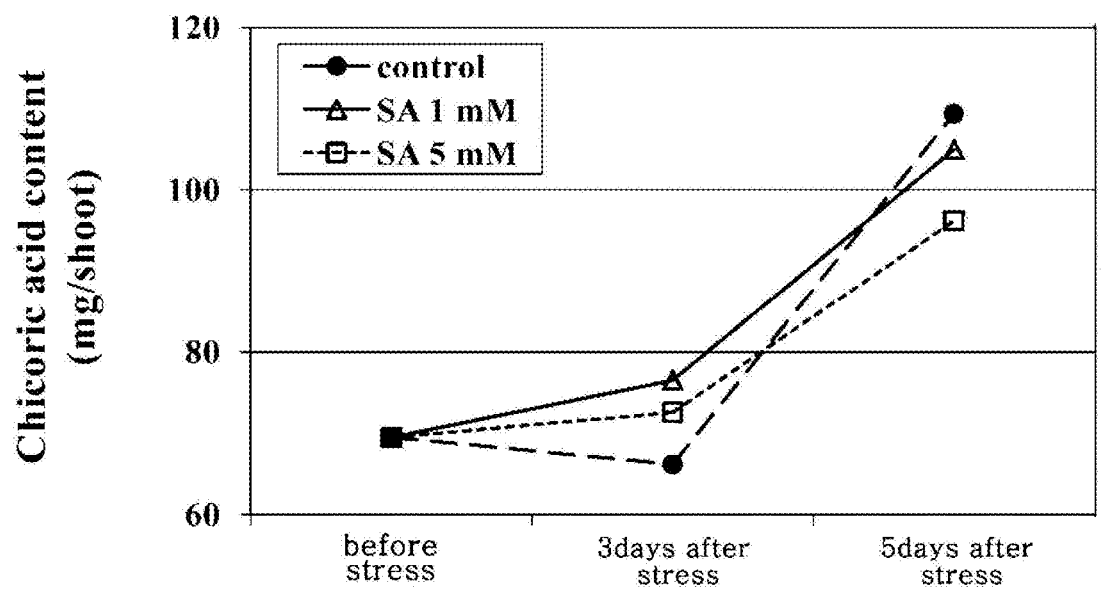

FIGS. 15A to 15C are graphs showing the total phenolic content, the antioxidant capacity, and the chicoric acid content calculated per plant, respectively. In FIGS. 15A to 15C, Control is a control group, SA 1 mM is *Crepidiastrum denticulatum* treated with 1 mM salicylic acid, and SA 5 mM is *Crepidiastrum denticulatum* treated with 5 mM salicylic acid.

As a result of exogenous treatment of salicylic acid at two concentrations, upon reviewing on the 3rd day after the treatment, the total phenolic content, the antioxidant capacity, the chicoric acid content increased in the treatment group with 1 mM salicylic acid.

As such, various external environmental stresses can be considered as being are capable of promoting the functional substances of *Crepidiastrum denticulatum* in a plant factory, which is a closed plant production system, to enable production of high-functional pharmaceutical-based plant raw materials, thereby achieving stable production and supply of the raw material.

Although certain exemplary embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

The invention claimed is:

1. A method for promoting growth and bioactive substances of *Crepidiastrum denticulatum*, the method comprising:
    performing a stress treatment on *Crepidiastrum denticulatum* during cultivation thereof, the stress treatment comprising at least one of applying visible light, drying, exposing to low temperature, irradiating ultraviolet rays, and applying a chemical elicitor.

2. The method of claim 1, wherein the stress treatment comprises applying visible light, the visible light is at least one of white light, red light, green light, and blue light.

3. The method of claim 2, wherein the visible light is one monochromatic light of red light, green light, and blue light.

4. The method of claim 2, wherein the visible light comprises mixed light having the ratio of at least one of:
    red light:blue light=6:4; red light:blue light=7:3; red light: blue light=8:2; red light:blue light=9:1; red light:green light:blue light=5:1:4; red light:green light:blue light=6:1:3; red light:green light:blue light=7:1:2; red light:green light:blue light=8:1:1; red light:green light: blue light=9:1:0; red light:green light:blue light=7:2:1; red light:white light:blue light=8:1:1; red light:white light:blue light=6:2:2; red light:white light:blue light=7:1:2; and red light:white light:blue light=8:2:0.

5. The method of claim 4, wherein the mixed light further comprises a far-red light.

6. The method of claim 5, wherein the mixed light comprises a red light and a blue light mixed at a ratio of 8:2.

7. The method of claim 6, wherein a ratio of the red light to the far-red light is at least one of 1.7, 1.2, 4.1, and 8.6 to 1.

8. The method of claim 5, further comprising harvesting *Crepidiastrum denticulatum* on the 6th week after planting *Crepidiastrum denticulatum*, when the mixed light comprising the far red light is applied during cultivation.

9. The method of claim 1, further comprising harvesting *Crepidiastrum denticulatum* on the 6th week after planting *Crepidiastrum denticulatum*, when the visible light is applied during cultivation.

10. The method of claim 1, wherein the stress treatment comprises drying, the drying comprises stop watering *Crepidiastrum denticulatum* for a predetermined period of time.

11. The method of claim 10, further comprising harvesting *Crepidiastrum denticulatum* on the $3^{rd}$ to $5^{th}$ days after the drying stress treatment.

12. The method of claim 1, wherein the stress treatment comprises drying, the drying comprises supplying water to *Crepidiastrum denticulatum* for a predetermined period of time using a wick.

13. The method of claim 12, further comprising harvesting *Crepidiastrum denticulatum* on the $2^{nd}$ day after the drying stress treatment.

14. The method of claim 1, wherein the stress treatment comprises exposing to low temperature, the low temperature stress treatment comprises exposing *Crepidiastrum denticulatum* at 10° C. during one of night time and day time.

15. The method of claim 1, wherein the stress treatment comprises exposing to low temperature, further comprising harvesting *Crepidiastrum denticulatum* on the $3^{rd}$ to $5^{th}$ days after the low temperature stress treatment.

16. The method of claim 1, wherein the stress treatment comprises irradiating ultraviolet rays, the ultraviolet rays comprises UV.

17. The method of claim 16, further comprising harvesting *Crepidiastrum denticulatum* 8 hours after UV-A is irradiated to *Crepidiastrum denticulatum*.

18. The method of claim 1, wherein the stress treatment comprises irradiating ultraviolet rays, the ultraviolet rays comprises UV-B.

19. The method of claim 18, further comprising harvesting *Crepidiastrum denticulatum* on the $2^{nd}$ day after UV-B is irradiated to *Crepidiastrum denticulatum*.

20. The method of claim 19, wherein UV-B is irradiated to *Crepidiastrum denticulatum* for 1 hour in every 11 hours during 2 days.

21. The method of claim 1, wherein the stress treatment comprises applying the chemical elicitor, the chemical elicitor comprises salicylic acid.

22. The method of claim 21, further comprising harvesting *Crepidiastrum denticulatum* on the $3^{rd}$ day after the chemical elicitor is sprayed onto *Crepidiastrum denticulatum*.

23. The method of claim 1, wherein *Crepidiastrum denticulatum* after the stress treatment has an increase in at least one of a shoot fresh weight, a shoot dry weight, number of leaves, a leaf area, a leaf length, and a leaf width of an aerial part.

24. The method of claim 1, wherein the bioactive substances of *Crepidiastrum denticulatum* promoted by the stress treatment comprise a phenolic compound and a chicoric acid.

* * * * *